US012620472B2

(12) United States Patent
Tanaka et al.

(10) Patent No.: US 12,620,472 B2
(45) Date of Patent: May 5, 2026

(54) METHOD, APPARATUS, AND PROGRAM FOR EVALUATION OF ANY ONE OR BOTH OF HEALTH STATE AND GROWTH STATE OF LIVESTOCK ANIMAL

(71) Applicant: AJINOMOTO CO., INC., Tokyo (JP)

(72) Inventors: Takayuki Tanaka, Kawasaki (JP); Yuko Susa, Kawasaki (JP); Tetsuya Takimoto, Kawasaki (JP); Yosuke Tsuneyoshi, Kawasaki (JP); Makoto Bannai, Kawasaki (JP)

(73) Assignee: AJINOMOTO CO. , INC., Tokyo (JP)

( * ) Notice: Subject to any disclaimer, the term of this patent is extended or adjusted under 35 U.S.C. 154(b) by 1103 days.

(21) Appl. No.: 17/061,156

(22) Filed: Oct. 1, 2020

(65) Prior Publication Data

US 2021/0020300 A1     Jan. 21, 2021

Related U.S. Application Data

(63) Continuation of application No. PCT/JP2019/014870, filed on Apr. 3, 2019.

(30) Foreign Application Priority Data

Apr. 10, 2018    (JP) ................................. 2018-075707

(51) Int. Cl.
| | |
|---|---|
| G01N 33/48 | (2006.01) |
| G06Q 30/0601 | (2023.01) |
| G06Q 50/02 | (2012.01) |
| G16H 10/40 | (2018.01) |
| G16H 15/00 | (2018.01) |
| G16H 20/60 | (2018.01) |
| G16H 50/20 | (2018.01) |
| G16H 50/30 | (2018.01) |

(52) U.S. Cl.
CPC ......... G16H 20/60 (2018.01); G06Q 30/0635 (2013.01); G06Q 50/02 (2013.01); G16H 10/40 (2018.01); G16H 15/00 (2018.01); G16H 50/20 (2018.01); G16H 50/30 (2018.01)

(58) Field of Classification Search
None
See application file for complete search history.

(56) References Cited

U.S. PATENT DOCUMENTS

| | | | |
|---|---|---|---|
| 7,827,015 | B2 | 11/2010 | McGoogan et al. |
| 7,904,284 | B2 | 3/2011 | Engelke et al. |
| 2004/0019434 | A1 | 1/2004 | Tedeschi et al. |
| 2005/0065736 | A1 | 3/2005 | Bauck et al. |
| 2005/0283347 | A1 | 12/2005 | Kimura et al. |
| 2006/0036419 | A1 | 2/2006 | Cook et al. |
| 2006/0041413 | A1 | 2/2006 | Burghardi et al. |
| 2006/0041419 | A1 | 2/2006 | Newcomb et al. |
| 2008/0154568 | A1 | 6/2008 | Burghardi et al. |
| 2008/0154569 | A1 | 6/2008 | McGoogan et al. |
| 2008/0183453 | A1 | 7/2008 | Engelke et al. |
| 2008/0189085 | A1 | 8/2008 | Cook et al. |
| 2008/0234995 | A1 | 9/2008 | Newcomb et al. |
| 2009/0234586 | A1 * | 9/2009 | Tanaka ............... G01N 33/6812 |
| | | | 702/179 |
| 2011/0010154 | A1 | 1/2011 | Cook et al. |
| 2016/0012748 | A1 | 1/2016 | Donavon |

FOREIGN PATENT DOCUMENTS

| | | |
|---|---|---|
| EP | 2 357 581 A2 | 8/2011 |
| JP | 2007-536609 | 12/2007 |
| JP | 2008-508606 | 3/2008 |
| JP | 2017-527264 | 9/2017 |
| WO | 2004/052191 A1 | 6/2004 |
| WO | 2008/016101 A1 | 2/2008 |
| WO | 2013/005790 A1 | 1/2013 |

OTHER PUBLICATIONS

Kim, Sung Woo, and Guoyao Wu. "Regulatory role for amino acids in mammary gland growth and milk synthesis." Amino acids 37 (2009): 89-95.*

Wu, Guoyao. "Functional amino acids in nutrition and health." Amino acids 45 (2013): 407-411.*

Li, Peng, et al. "Dietary supplementation with cholesterol and docosahexaenoic acid affects concentrations of amino acids in tissues of young pigs." Amino Acids 37.4 (2009): 709-716.*

Extended European Search Report issued Dec. 2, 2021 in European Patent Application No. 19785459.9, 9 pages.

International Search Report in Application No. PCT/JP2019/014870 issued Jul. 9, 2019.

Tsukahara, T, "Estimation of amino acid and other nutrient components required for growth of underdeveloped pig on the basis of difference between artery and vein", Examination performance report on grant-in-aid research for meat, (2017), vol. 35, pp. 395-400.

Shibano, K et al., "Blood Amino Acid Concentration in Japanese Black Calves of Different Daily Gains and Effects of Administration of an Amino Acid Preparation", Journal of livestock medicine), (2012), vol. 59, No. 11, pp. 685-696.

(Continued)

*Primary Examiner* — Anna Skibinsky

(74) *Attorney, Agent, or Firm* — Oblon, McClelland, Maier & Neustadt, L.L.P.

(57)     ABSTRACT

An information processing method, which includes an evaluating step of evaluating at least one item of growth potential, nutrition state of a protein, utilization efficiency of an amino acid, glucose metabolism, stress, appetite, feed efficiency, growth speed, and growth prediction, by using a blood concentration value of at least one amino acid of Asn, Ser, Gly, His, Thr, Arg, Pro, Tyr, Val, Met, Orn, Lys, Ile, Leu, Phe, Trp, and 3Met-His, obtained from an animal, or a value of one or a plurality of formulae that include an explanatory variable to be substituted with the blood concentration value, calculated using the formula and the blood concentration value, wherein at the evaluating step, each evaluation is carried out using the blood concentration value or the value of one formula, is useful for evaluating the health and/or growth state of livestock.

21 Claims, 14 Drawing Sheets

(56)                    References Cited

OTHER PUBLICATIONS

Proenza, A. M. et al., "Gender related difference in the effect of aging on blood amino acid compartmentation", Journal of Nutritional Biochemistry, (2001), vol. 12, pp. 431-440.

Mohmad-Saberi, S. E. et al., "Metabolomics profiling of extracellular metabolites in CHO-K1 cells cultured in different types of growth media", Cytotechnology, (2013), vol. 65, pp. 577-586.

Cervantes, M. et al., "Serum concentrations of free amino acids in growing pigs exposed to diurnal heat stress fluctuations", Journal of Thermal Biology, (2017), vol. 69, pp. 69-75.

A.J. van Dijk et al., "Growth performance of weanling pigs fed spray-dried animal plasma a review, Livestock Production", Science, (2001), 68, 2-3, 263-274.

Robert D. Goodband et al., "General Nutrition Principles for Swine" (Oct. 1997).

Grandin, T, "The effect of stress onlivestock and meat quality prior to and during slaughter", International Journal for the Study of Animal Problems, (1980), 1(5), 313-337.

John F. Patience, et al., "A review of feed efficiency in swine: biology and application", J Anim Sci Biotechnol, (2015), 6(1), 33.

Guoyao Wu et al., "Arginine metabolism and nutrition in growth, health and disease", Amino Acids (2009) 37: 153-168.

* cited by examiner (BASIC PRINCIPLE OF THE INVENTION)

(BASIC PRINCIPLE OF THE INVENTION)

| INDIVIDUAL IDENTIFICA-TION INFORMATION | ENVIRONMENT IDENTIFICA-TION INFORMATION | CUSTOMER IDENTIFICA-TION INFORMATION | CONCENTRATION DATA | | | | | |
|---|---|---|---|---|---|---|---|---|
| | | | Gly | Leu | Val | Ile | Phe | ... |
| I-1 | G-1 | C-1 | 9.5 | 11.2 | 2.7 | 8.5 | 4.9 | ... |
| I-2 | G-2 | C-2 | 8.5 | 10.5 | 3.9 | 9.8 | 6.1 | ... |
| ⋮ | ⋮ | ⋮ | ⋮ | ⋮ | ⋮ | ⋮ | ⋮ | ⋮ |

FIG.6

| INDIVIDUAL IDENTIFI-CATION INFORMA-TION | INDEX DATA | | | | | | | | | CONCENTRATION DATA | | | | | | |
|---|---|---|---|---|---|---|---|---|---|---|---|---|---|---|---|---|
| | IGF-1 | ALB | 3Met-His | INSULIN | Trp/Kyn | ADFI | G:F | ΔBODY LENGTH | LATE REARING BODY WEIGHT | Gly | Leu | Val | Ile | Phe | ... |
| I-1 | ... | ... | ... | ... | ... | ... | ... | | | 9.5 | 11.2 | 2.7 | 8.5 | 4.9 | ... |
| I-2 | ... | ... | ... | ... | ... | ... | ... | | | 8.5 | 10.5 | 3.9 | 9.8 | 6.1 | ... |
| ... | | | | | | | | | | | | | | | |

| INDIVIDUAL IDENTIFICATION INFORMATION | INDEX DATA | CONCENTRATION DATA | | | |
|---|---|---|---|---|---|
| | IGF-1 | Gly | Leu | Val | ... |
| I-1 | | 9.5 | 11.2 | 4.9 | ... |
| I-2 | | 8.5 | 10.5 | 6.1 | ... |
| ⋮ | ⋮ | ⋮ | ⋮ | ⋮ | ⋮ |

| RANK | FORMULA | THRESHOLD VALUE | INSPECTION RESULT | ITEM IDENTIFICATION INFORMATION |
|---|---|---|---|---|
| 1 | | | | |
| 2 | | | | |
| 3 | | | | |
| ⋮ | ⋮ | ⋮ | ⋮ | ⋮ |

FIG.9

| INDIVIDUAL IDENTIFI-CATION INFORMATION | ENVIRONMENT IDENTIFI-CATION INFORMATION | CUSTOMER IDENTIFI-CATION INFORMATION | CALCULATION RESULT DATA | | | | | | | | | |
|---|---|---|---|---|---|---|---|---|---|---|---|---|
| | | | GROWTH POTENTIAL | NUTRITION STATE OF PROTEIN | UTILIZATION EFFICIENCY OF AMINO ACID | GLUCOSE METABOLISM | STRESS | APPETITE | FEED EFFICIENCY | GROWTH SPEED | GROWTH PREDICTION |
| I-1 | G-1 | C-1 | | | | | | | | | |
| ... | ... | ... | ... | ... | ... | ... | ... | ... | ... | ... | ... |

| INDIVIDUAL IDENTIFICATION INFORMATION | ENVIRONMENT IDENTIFICATION INFORMATION | CUSTOMER IDENTIFICATION INFORMATION | EVALUATION RESULT DATA | | | | | | | | | | | | | RESULT DATA |
|---|---|---|---|---|---|---|---|---|---|---|---|---|---|---|---|---|
| | | | GROWTH POTENTIAL | NUTRITION STATE OF PROTEIN | UTILIZATION EFFICIENCY OF AMINO ACID | GLUCOSE METABOLISM | STRESS | APPETITE | FEED EFFICIENCY | GROWTH SPEED | GROWTH PREDICTION | NUTRITION STATE | GROWTH | PHYSIOLOGICAL RESPONSE | | |
| I-1 | G-1 | C-1 | e.g.) EVALUATION CLASS ("GOOD" "IN-BETWEEN" "NOT GOOD"), EVALUATED VALUE | | | | | | | | | | | | |
| ... | ... | ... | ... | ... | ... | ... | ... | ... | ... | ... | ... | ... | ... | ... | ... |

| ITEM IDENTIFICATION INFORMATION | RECOMMENDABLE AMINO ACID |
|---|---|
| GROWTH POTENTIAL | BCAA(Val,Leu,Ile),Arg,Glu,Gln |
| NUTRITION STATE OF PROTEIN | BCAA(Val,Leu,Ile),Arg,Glu,Gln |
| UTILIZATION EFFICIENCY OF AMINO ACID | BCAA(Val,Leu,Ile) |
| GLUCOSE METABOLISM | BCAA(Val,Leu,Ile),Arg,Glu,Gln |
| STRESS | Trp,Phe,Tyr |
| APPETITE | Trp,Phe,Tyr |
| FEED EFFICIENCY | BCAA(Val,Leu,Ile),Arg,Glu,Gln,Trp,Phe,Tyr |
| GROWTH SPEED | BCAA(Val,Leu,Ile),Arg,Glu,Gln,Trp,Phe,Tyr |
| GROWTH PREDICTION | BCAA(Val,Leu,Ile),Arg,Glu,Gln,Trp,Phe,Tyr |
| NUTRITION STATE | BCAA(Val,Leu,Ile),Arg,Glu,Gln |
| GROWTH | BCAA(Val,Leu,Ile),Arg,Glu,Gln,Trp,Phe,Tyr |
| PHYSIOLOGICAL RESPONSE | Trp,Phe,Tyr |

| INDIVIDUAL IDENTIFI-CATION INFORMATION | ENVIRONMENT IDENTIFI-CATION INFORMATION | CUSTOMER IDENTIFI-CATION INFORMATION | RECOMMEND-ABLE AMINO ACID |
|---|---|---|---|
| I-1 | G-1 | C-1 | |
| ⋮ | ⋮ | ⋮ | ⋮ |

| CUSTOMER IDENTIFICATION INFORMATION | ORDERING DESTINATION IDENTIFICATION INFORMATION | ORDERING DATA | | | |
|---|---|---|---|---|---|
| | | ORDERING DATE | GOOD | NUMBER | MANUFAC-TURER |
| C-1 | S-1 | | | | |
| ⋮ | ⋮ | ⋮ | ⋮ | ⋮ | ⋮ |

| INDIVIDUAL IDENTIFICATION INFORMATION | ENVIRONMENT IDENTIFICATION INFORMATION | CUSTOMER IDENTIFICATION INFORMATION | OPINION DATA |
|---|---|---|---|
| I-1 | G-1 | C-1 | |
| ⋮ | ⋮ | ⋮ | ⋮ |

| ITEM IDENTIFICATION INFORMATION | ENVIRONMENT IDENTIFICATION INFORMATION |
|---|---|
| | G-1 |
| GROWTH POTENTIAL | e.g.) EVALUATION CLASS ("GOOD" "IN-BETWEEN" "NOT GOOD"), EVALUATED VALUE |
| NUTRITION STATE OF PROTEIN | |
| UTILIZATION EFFICIENCY OF AMINO ACID | |
| GLUCOSE METABOLISM | |
| STRESS | |
| APPETITE | |
| FEED EFFICIENCY | |
| GROWTH SPEED | |
| GROWTH PREDICTION | |

FIG.18

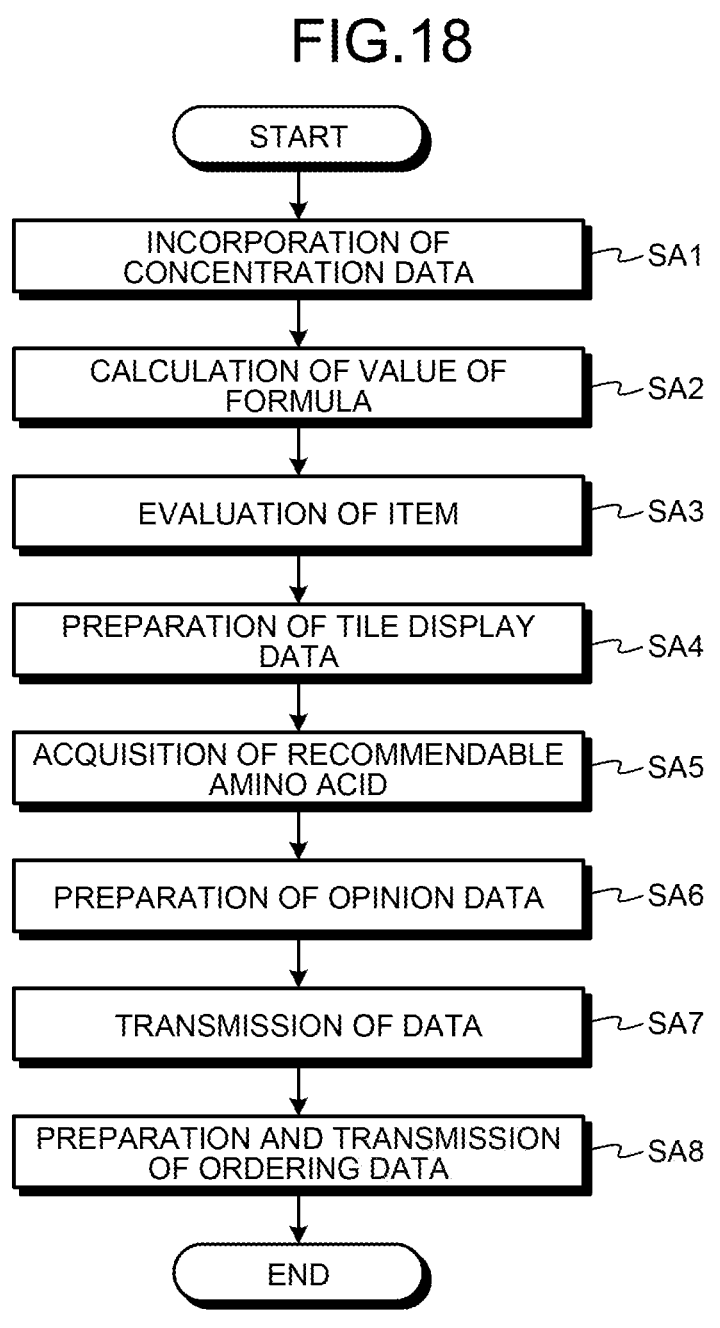

START

INCORPORATION OF CONCENTRATION DATA ~SA1

CALCULATION OF VALUE OF FORMULA ~SA2

EVALUATION OF ITEM ~SA3

PREPARATION OF TILE DISPLAY DATA ~SA4

ACQUISITION OF RECOMMENDABLE AMINO ACID ~SA5

PREPARATION OF OPINION DATA ~SA6

TRANSMISSION OF DATA ~SA7

PREPARATION AND TRANSMISSION OF ORDERING DATA ~SA8

END

METHOD, APPARATUS, AND PROGRAM FOR EVALUATION OF ANY ONE OR BOTH OF HEALTH STATE AND GROWTH STATE OF LIVESTOCK ANIMAL

CROSS REFERENCES TO RELATED APPLICATIONS

This application is a continuation of International Patent Application No. PCT/JP2019/014870, filed Apr. 3, 2019, and claims priority to Japanese Patent Application No. 2018-075707, filed Apr. 10, 2018, both of which are incorporated herein by reference in their entireties.

BACKGROUND OF THE INVENTION

Field of the Invention

The present invention relates to information processing methods calculating methods, information processing apparatus, calculating apparatus, information processing programs, and calculating programs.

Discussion of the Background

In an animal husbandry field, it is increasingly required to actively deal with new issues that require some costs (for example, prevention measures against epidemic and disease so as to reduce an accident rate and deal with an animal welfare) as a part of social responsibilities, in addition to improvement in productivity (for example, shortening of rearing days and increase in a feed utilization efficiency). In order to deal with these new issues, too, a healthy and good livestock animal with a decreased disease risk needs to be reared; thus, realization of a further rational rearing environment (for example, precise grasping of a health state of a livestock animal) is important.

A test of a biomarker to indicate a health state is rapidly advancing because of a recent development in a genome analysis and a post-genome test. Also, the biomarker is being widely used in prevention, diagnosis, prognosis prediction, and the like of a disease. Biomarkers actively tested are on the bases of: a genomics and transcriptomics based on gene information; a proteomics based on protein information; and a metabolomics based on metabolic information.

However, in the biomarkers based on the genomics and the transcriptomics, there is a problem in that an environmental factor is not reflected even though a genetic factor is reflected. In the biomarker based on the proteomics, because it is necessary to analyze many proteins, there is a problem in that many problems are still remained unsolved in the analysis methods as well as the comprehensive analysis method thereof. In the biomarker based on the metabolomics, there may be a promising future as the biomarker that reflects not only a genetic factor but also an environmental factor; but because there are so many metabolites, there is a problem in that many problems are still remained unsolved in the comprehensive analysis method thereof.

Existing biomarkers indicating a health state of a pig that have been reported are: a blood IGF-1 (Insulin-like Growth Factor-1) indicating a secretion amount of a growth hormone (see A. J. van Dijk, H. Everts, M. J. A. Nabuurs, R. J. C. F. Margry, A. C. Beynen, Growth performance of weanling pigs fed spray-dried animal plasma: a review, Livestock Production Science, 2001, 68, 2-3, 263-274, which is incorporated herein by reference in its entirety); a blood insulin indicating a metabolic state of a glucose (see A. J. van Dijk, H. Everts, M. J. A. Nabuurs, R. J. C. F. Margry, A. C. Beynen, Growth performance of weanling pigs fed spray-dried animal plasma: a review, Livestock Production Science, 2001, 68, 2-3, 263-274, which is incorporated herein by reference inits entirety); a blood albumin indicating a nutrition state of a protein (see Robert D. Goodband, Mike D. Tokach, Steve S. Dritz, Jim L. Nelssen, General Nutrition Principles for Swine, Kansas State University Agricultural Experiment Station and Cooperative Extension Service, 1997, which is incorporated herein by reference in its entirety); and a blood serotonin as well as kynurenine and tryptophan, the neighboring metabolites of serotonin, indicating a stress state (see Grandin, T, The effect of stress on livestock and meat quality prior to and during slaughter, International Journal for the Study of Animal Problems, 1980, 1(5), 313-337, which is incorporated herein by reference in its entirety). Existing biomarkers indicating a growth state of a pig that have been reported are: Average Daily Feed Intake (see John F. Patience, Mariana C. Rossoni-Serao, Nestor A. Gutierrez, A review of feed efficiency in swine: biology and application, J Anim Sci Biotechnol, 2015, 6(1), 33, which is incorporated herein by reference in its entirety) and Gain to Feed Ratio (see John F. Patience, Mariana C. Rossoni-Serao, Nestor A. Gutierrez, A review of feed efficiency in swine: biology and application, J Anim Sci Biotechnol, 2015, 6(1), 33, which is incorporated herein by reference in its entirety).

JP-T-2017-527264, which is incorporated herein by reference in its entirety, discloses, among others, a system to provide advices with regard to nutrition, health, and/or wellness of an animal on the basis of the data obtained by collecting and analyzing at least one parameter that relates to health, diet therapy, action, and environment of the animal. JP-T-2008-508606, which is incorporated herein by reference in its entirety, discloses, among others, a system to generate an animal feed blend based on utilization of nutrition elements to be ingested by the animal. JP-T-2007-536609, which is incorporated herein by reference in its entirety, discloses, among others, a method assisted with a computer to trace bleeding and treatment of an animal doctor thereby correlating these data with expression data formed by a SNP-based gene type and with capacity data relating to a livestock animal. US-A-2004/0019434, which is incorporated herein by reference in its entirety, discloses, among others, a method to predict a feed requirement to an individual animal and a feed efficiency thereof.

However, the biomarkers described in A. J. van Dijk, H. Everts, M. J. A. Nabuurs, R. J. C. F. Margry, A. C. Beynen, Growth performance of weanling pigs fed spray-dried animal plasma: a review, Livestock Production Science, 2001, 68, 2-3, 263-274; Robert D. Goodband, Mike D. Tokach, Steve S. Dritz, Jim L. Nelssen, General Nutrition Principles for Swine, Kansas State University Agricultural Experiment Station and Cooperative Extension Service, 1997; and Grandin, T, The effect of stress onlivestock and meat quality prior to and during slaughter, International Journal for the Study of Animal Problems, 1980, 1(5), 313-337, all of which are incorporated herein by reference in their entireties, require a plurality of dedicated analysis kits. The growth indicator described in John F. Patience, Mariana C. Rossoni-Serao, Nestor A. Gutierrez, A review of feed efficiency in swine: biology and application, J Anim Sci Biotechnol, 2015, 6(1), 33, which is incorporated herein by reference in its entirety, requires actual measurement of a pig weight after it is guided to a weighing machine and the weight thereof is revised. Therefore, there has been a problem in that a technology has not yet been developed to satisfy requirements of a farmer or an animal doctor to conveniently and objectively grasp a health state and/or a growth state of an animal (specifically, a livestock animal such as a pig).

SUMMARY OF THE INVENTION

Accordingly, it is one object of the present invention to at least partially solve the problems in the conventional technology.

It is another object of the present invention to provide novel information processing methods, calculating methods, information processing apparatus, calculating apparatus, information processing programs, and calculating programs which can provide a person involved in an animal (for example, a livestock animal such as a pig) with sufficiently reliable information so that the person (for example, a farmer and an animal doctor when the animal is a livestock animal) can conveniently and objectively grasp any one or both of a health state and a growth state of the animal thereby contributing to realization of a rational rearing environment of the animal.

These and other objects, which will become apparent during the following detailed description, have been achieved by the information processing method, which according to one aspect of the present disclosure, includes an evaluating step of evaluating at least one item of 9 items (growth potential, nutrition state of a protein, utilization efficiency of an amino acid, glucose metabolism, stress, appetite, feed efficiency, growth speed, and growth prediction) by using a blood concentration value of at least one amino acid of 17 kinds of amino acids (Asn, Ser, Gly, His, Thr, Arg, Pro, Tyr, Val, Met, Orn, Lys, Ile, Leu, Phe, Trp, and 3Met-His), obtained from an animal, or a value of one or a plurality of formulae that include an explanatory variable to be substituted with the blood concentration value, calculated using the formula and the blood concentration value, wherein at the evaluating step, each evaluation is carried out using the blood concentration value or the value of one formula.

In the present specification, various amino acids are mainly written in abbreviations, the formal names of these are as follows.

| Abbreviation | Formal name |
|---|---|
| Ala | Alanine |
| Arg | Arginine |
| Asn | Asparagine |
| Cit | Citrulline |
| Gln | Glutamine |
| Gly | Glycine |
| His | Histidine |
| Ile | Isoleucine |
| Leu | Leucine |
| Lys | Lysine |
| Met | Methionine |
| Orn | Ornithine |
| Phe | Phenylalanine |
| Pro | Proline |
| Ser | Serine |
| Tau | Taurine |
| Thr | Threonine |
| Trp | Tryptophan |
| Tyr | Tyrosine |
| Val | Valine |
| 3Met-His | 3Methyl-Histidine |

In the information processing method according to another aspect of the present disclosure, at the evaluating step, (1) evaluation of the growth potential is carried out by using a blood concentration value of at least one amino acid of Asn, Gly, Pro, Tyr, Lys, Ile, Leu, and Trp, or a value of a formula that includes an explanatory variable to be substituted with the blood concentration value, calculated using the formula and the blood concentration value; (2) evaluation of the nutrition state of a protein is carried out by using a blood concentration value of at least one amino acid of His, Arg, Tyr, Val, Lys, Ile, Leu, Phe, and Trp, or a value of a formula that includes an explanatory variable to be substituted with the blood concentration value, calculated using the formula and the blood concentration value; (3) evaluation of the utilization efficiency of an amino acid is carried out by using a blood concentration value of His, or a value of a formula that includes an explanatory variable to be substituted with the blood concentration value, calculated using the formula and the blood concentration value; (4) evaluation of the glucose metabolism is carried out by using a blood concentration value of at least one amino acid of Thr, Arg, Tyr, Met, Orn, and Phe, or a value of a formula that includes an explanatory variable to be substituted with the blood concentration value, calculated using the formula and the blood concentration value; (5) evaluation of the stress is carried out by using a blood concentration value of at least one amino acid of Ser, Tyr, Ile, and Trp, or a value of a formula that includes an explanatory variable to be substituted with the blood concentration value, calculated using the formula and the blood concentration value; (6) evaluation of the appetite is carried out by using a blood concentration value of Trp, or a value of a formula that includes an explanatory variable to be substituted with the blood concentration value, calculated using the formula and the blood concentration value; (7) evaluation of the feed efficiency is carried out by using a blood concentration value of 3Met-His, or a value of a formula that includes an explanatory variable to be substituted with the blood concentration value, calculated using the formula and the blood concentration value; (8) evaluation of the growth speed is carried out by using a blood concentration value of at least one amino acid of Pro, Tyr, Lys, Ile, Leu, and Trp, or a value of a formula that includes an explanatory variable to be substituted with the blood concentration value, calculated using the formula and the blood concentration value; and (9) evaluation of the growth prediction is carried out by using a blood concentration value of at least one amino acid of Arg, Tyr, Ile, Phe, and Trp, or a value of a formula that includes an explanatory variable to be substituted with the blood concentration value, calculated using the formula and the blood concentration value.

In the information processing method according to still another aspect of the present disclosure, at the evaluating step, on the basis of the evaluation results of these items, at least one item of 3 items (nutrition state, growth, and physiological response) is further evaluated, wherein at the evaluating step, evaluation of the nutrition state is carried out on the basis of the evaluation result of the growth potential and the evaluation result of the nutrition state of a protein; evaluation of the growth is carried out on the basis of the evaluation result of the growth speed and the evaluation result of the growth prediction; and evaluation of the physiological response is carried out on the basis of the evaluation result of the stress.

In the information processing method according to still another aspect of the present disclosure, a rearing environment of the animal is evaluated. In the information processing method according to still another aspect of the present disclosure, the animal is a livestock animal. In the information processing method according to still another aspect of the present disclosure, the livestock animal is a pig. In the information processing method according to still another aspect of the present disclosure, the blood concentration value is of an artificial lactation period. In the information processing method according to still another aspect of the present disclosure, the blood concentration value thereof is of the daily age of 45 days to 60 days.

In the information processing method according to still another aspect of the present disclosure, the evaluating step is carried out in a control unit of an information processing apparatus including the control unit.

The information processing method according to still another aspect of the present disclosure includes a setting step of setting, item by item, any one or both of a color and a pattern corresponding to an evaluation result of the item; and a first result data preparing step of preparing the result data with regard to a tile display of a rectangular area of each item, in which any one or both of the color and the pattern in the area are those having been set at the setting step and a character string corresponding to the respective items is disposed in the area, wherein the setting step and the first result data preparing step are carried out in the control unit.

The information processing method according to still another aspect of the present disclosure includes a second result data preparing step of preparing the result data with regard to the evaluation results of the items displayed in a table style or in a list style, wherein the second result data preparing step is carried out in the control unit.

The information processing method according to still another aspect of the present disclosure includes an acquiring step of acquiring, from the recommendable amino acid data including recommendable amino acids in each item, the amino acids being recommended to improve the evaluation result of the item, a recommendable amino acid corresponding to the item resulting in the unfavorable evaluation, wherein the acquiring step is carried out in the control unit.

In the information processing method according to still another aspect of the present disclosure, the recommendable amino acid data include, as the recommendable amino acid, at least one amino acid of Met, Lys, Thr, Trp, Val, Leu, Ile, Arg, Tyr, Phe, Gln, Glu, Gly, Cys2, and His.

In the information processing method according to still another aspect of the present disclosure, the information processing apparatus is connected through a communicable network to an information processing apparatus of a company that sells amino acids, wherein the method includes an ordering data preparing step of preparing ordering data of the recommendable amino acid acquired at the acquiring step; and an ordering data transmitting step of transmitting the ordering data prepared at the ordering data preparing step to the information processing apparatus of the company, wherein the ordering data preparing step and the ordering data transmitting step are carried out in the control unit.

The information processing method according to still another aspect of the present disclosure includes an opinion data preparing step of preparing, on the basis of the evaluation results of the items, opinion data in order to improve a rearing condition of an animal, wherein the opinion data preparing step is carried out in the control unit.

A calculating method according to one aspect of the present disclosure includes a calculating step of calculating a value of one or a plurality of 9 formulae (a formula to evaluate the growth potential, a formula to evaluate the nutrition state of a protein, a formula to evaluate the utilization efficiency of an amino acid, a formula to evaluate the glucose metabolism, a formula to evaluate the stress, a formula to evaluate the appetite, a formula to evaluate the feed efficiency, a formula to evaluate the growth speed, and a formula to evaluate the growth prediction) that include an explanatory variable to be substituted with a blood concentration value of at least one amino acid of the 17 kinds of amino acids, obtained from an animal, the value being calculated using the formula and the blood concentration value.

In the calculating method according to another aspect of the present disclosure, at the calculating step, (1) a value of the formula to evaluate the growth potential is calculated using a blood concentration value of at least one amino acid of Asn, Gly, Pro, Tyr, Lys, Ile, Leu, and Trp, and the formula that includes an explanatory variable to be substituted with the blood concentration value; (2) a value of the formula to evaluate the nutrition state of a protein is calculated using a blood concentration value of at least one amino acid of His, Arg, Tyr, Val, Lys, Ile, Leu, Phe, and Trp, and the formula that includes an explanatory variable to be substituted with the blood concentration value; (3) a value of the formula to evaluate the utilization efficiency of an amino acid is calculated using a blood concentration value of His and the formula that includes an explanatory variable to be substituted with the blood concentration value; (4) a value of the formula to evaluate the glucose metabolism is calculated using a blood concentration value of at least one amino acid of Thr, Arg, Tyr, Met, Orn, and Phe, and the formula that includes an explanatory variable to be substituted with the blood concentration value; (5) a value of the formula to evaluate the stress is calculated using a blood concentration value of at least one amino acid of Ser, Tyr, Ile, and Trp, and the formula that includes an explanatory variable to be substituted with the blood concentration value; (6) a value of the formula to evaluate the appetite is calculated using a blood concentration value of Trp and the formula that includes an explanatory variable to be substituted with the blood concentration value; (7) a value of the formula to evaluate the feed efficiency is calculated using a blood concentration value of 3Met-His and the formula that includes an explanatory variable to be substituted with the blood concentration value; (8) a value of the formula to evaluate the growth speed is calculated using a blood concentration value of at least one amino acid of Pro, Tyr, Lys, Ile, Leu, and Trp, and the formula that includes an explanatory variable to be substituted with the blood concentration value; and (9) a value of the formula to evaluate the growth prediction is calculated using a blood concentration value of at least one amino acid of Arg, Tyr, Ile, Phe, and Trp, and the formula that includes an explanatory variable to be substituted with the blood concentration value.

In the calculating method according to still another aspect of the present disclosure, the calculating step is carried out in a control unit of an information processing apparatus including the control unit.

An information processing apparatus according to one aspect of the present disclosure includes a control unit, wherein the control unit includes an evaluating unit that evaluates at least one item of the 9 items by using a blood concentration value of at least one amino acid of the 17 kinds of amino acids, obtained from an animal, or a value of one or a plurality of formulae that include an explanatory variable to be substituted with the blood concentration value, calculated using the formula and the blood concentration value, wherein the evaluating unit carries out each evaluation using the blood concentration value or the value of one formula.

In an information processing apparatus according to another aspect of the present disclosure, the evaluation unit (1) carries out evaluation of the growth potential by using a blood concentration value of at least one amino acid of Asn, Gly, Pro, Tyr, Lys, Ile, Leu, and Trp, or a value of a formula that includes an explanatory variable to be substituted with the blood concentration value, calculated using the formula and the blood concentration value; (2) carries out evaluation of the nutrition state of a protein by using a blood concentration value of at least one amino acid of His, Arg, Tyr, Val, Lys, Ile, Leu, Phe, and Trp, or a value of a formula that includes an explanatory variable to be substituted with the blood concentration value, calculated using the formula and the blood concentration value; (3) carries out evaluation of the utilization efficiency of an amino acid by using a blood concentration value of His, or a value of a formula that includes an explanatory variable to be substituted with the blood concentration value, calculated using the formula and the blood concentration value; (4) carries out evaluation of the glucose metabolism by using a blood concentration value of at least one amino acid of Thr, Arg, Tyr, Met, Orn, and Phe, or a value of a formula that includes an explanatory variable to be substituted with the blood concentration value, calculated using the formula and the blood concentration value; (5) carries out evaluation of the stress by using a blood concentration value of at least one amino acid of Ser, Tyr, Ile, and Trp, or a value of a formula that includes an explanatory variable to be substituted with the blood concentration value, calculated using the formula and the blood concentration value; (6) carries out evaluation of the appetite by using a blood concentration value of Trp, or a value of a formula that includes an explanatory variable to be substituted with the blood concentration value, calculated using the formula and the blood concentration value; (7) carries out evaluation of the feed efficiency by using a blood concentration value of 3Met-His, or a value of a formula that includes an explanatory variable to be substituted with the blood concentration value, calculated using the formula and the blood concentration value; (8) carries out evaluation of the growth speed by using a blood concentration value of at least one amino acid of Pro, Tyr, Lys, Ile, Leu, and Trp, or a value of a formula that includes an explanatory variable to be substituted with the blood concentration value, calculated using the formula and the blood concentration value; and (9) carries out evaluation of the growth prediction by using a blood concentration value of at least one amino acid of Arg, Tyr, Ile, Phe, and Trp, or a value of a formula that includes an explanatory variable to be substituted with the blood concentration value, calculated using the formula and the blood concentration value.

In the information processing method according to still another aspect of the present disclosure, on the basis of the evaluation results of these items, the evaluating unit further evaluates at least one item of the 3 items, wherein the evaluating unit carries out evaluation of the nutrition state on the basis of the evaluation result of the growth potential and the evaluation result of the nutrition state of a protein; carries out evaluation of the growth on the basis of the evaluation result of the growth speed and the evaluation result of the growth prediction; and carries out evaluation of the physiological response on the basis of the evaluation result of the stress.

In the information processing apparatus according to still another aspect of the present disclosure, a rearing environment of the animal is evaluated. In the information processing apparatus according to still another aspect of the present disclosure, the animal is a livestock animal. In the information processing apparatus according to still another aspect of the present disclosure, the livestock animal is a pig. In the information processing apparatus according to still another aspect of the present disclosure, the blood concentration value is of an artificial lactation period. In the information processing apparatus according to still another aspect of the present disclosure, the blood concentration value thereof is of the daily age of 45 days to 60 days.

In the information processing apparatus according to still another aspect of the present disclosure, the control unit includes a setting unit that sets, item by item, any one or both of a color and a pattern corresponding to evaluation result of the item; and a first result data preparing unit prepares the result data with regard to a tile display of a rectangular area of each item, in which any one or both of the color and the pattern in the area are those having been set by the setting unit and a character string corresponding to the respective items is disposed in the area.

In the information processing apparatus according to still another aspect of the present disclosure, the control unit includes a second result data preparing unit that prepares the result data with regard to the evaluation results of the items displayed in a table style or in a list style.

In the information processing apparatus according to still another aspect of the present disclosure, the control unit includes an acquiring unit that acquires, from the recommendable amino acid data including recommendable amino acids in each item, the amino acids being recommended to improve the evaluation result of the item, a recommendable amino acid corresponding to the item resulting in the unfavorable evaluation.

In the information processing apparatus according to still another aspect of the present disclosure, the recommendable amino acid data include, as the recommendable amino acid, at least one amino acid of Met, Lys, Thr, Trp, Val, Leu, Ile, Arg, Tyr, Phe, Gln, Glu, Gly, Cys2, and His.

The information processing apparatus according to still another aspect of the present disclosure is connected through a communicable network to an information processing apparatus of a company that sells amino acids, wherein the control unit includes an ordering data preparing unit that prepares ordering data of the recommendable amino acid acquired by the acquiring unit; and an ordering data transmitting unit that transmits the ordering data prepared by the ordering data preparing unit to the information processing apparatus of the company.

In the information processing apparatus according to still another aspect of the present disclosure, the control unit includes an opinion data preparing unit that prepares, on the basis of the evaluation results of the items, opinion data in order to improve a rearing condition of an animal.

A calculating apparatus according to one aspect of the present disclosure includes a control unit, wherein the control unit includes a calculating unit that calculates a value of one or a plurality of the 9 formulae that include an explanatory variable to be substituted with a blood concentration value of at least one amino acid of the 17 kinds of amino acids, obtained from an animal, the value being calculated using the formula and the blood concentration value.

In the calculating apparatus according to another aspect of the present disclosure, the calculating unit (1) calculates a value of the formula to evaluate the growth potential using a blood concentration value of at least one amino acid of Asn, Gly, Pro, Tyr, Lys, Ile, Leu, and Trp, and the formula that includes an explanatory variable to be substituted with the blood concentration value; (2) calculates a value of the formula to evaluate the nutrition state of a protein using a blood concentration value of at least one amino acid of His, Arg, Tyr, Val, Lys, Ile, Leu, Phe, and Trp, and the formula that includes an explanatory variable to be substituted with the blood concentration value; (3) calculates a value of the formula to evaluate the utilization efficiency of an amino acid using a blood concentration value of His and the formula that includes an explanatory variable to be substituted with the blood concentration value; (4) calculates a value of the formula to evaluate the glucose metabolism using a blood concentration value of at least one amino acid of Thr, Arg, Tyr, Met, Orn, and Phe, and the formula that includes an explanatory variable to be substituted with the blood concentration value; (5) calculates a value of the formula to evaluate the stress using a blood concentration value of at least one amino acid of Ser, Tyr, Ile, and Trp, and the formula that includes an explanatory variable to be substituted with the blood concentration value; (6) calculates a value of the formula to evaluate the appetite using a blood concentration value of Trp and the formula that includes an explanatory variable to be substituted with the blood concentration value; (7) calculates a value of the formula to evaluate the feed efficiency using a blood concentration value of 3Met-His and the formula that includes an explanatory variable to be substituted with the blood concentration value; (8) calculates a value of the formula to evaluate the growth speed using a blood concentration value of at least one amino acid of Pro, Tyr, Lys, Ile, Leu, and Trp, and the formula that includes an explanatory variable to be substituted with the blood concentration value; and (9) calculates a value of the formula to evaluate the growth prediction using a blood concentration value of at least one amino acid of Arg, Tyr, Ile, Phe, and Trp, and the formula that includes an explanatory variable to be substituted with the blood concentration value.

An information processing program product according to one aspect of the present disclosure has a non-transitory tangible computer readable medium including programmed instructions for causing a control unit of an information processing apparatus including the control unit to carry out an information processing method, wherein the information processing method includes an evaluating step of evaluating at least one item of the 9 items by using a blood concentration value of at least one amino acid of the 17 kinds of amino acids, obtained from an animal, or a value of one or a plurality of formulae that include an explanatory variable to be substituted with the blood concentration value, calculated using the formula and the blood concentration value, wherein at the evaluating step, each evaluation is carried out using the blood concentration value or the value of one formula.

A calculating program product having a non-transitory tangible computer readable medium including programmed instructions for causing a control unit of an information processing apparatus including the control unit to carry out a calculating method, wherein the calculating method includes a calculating step of calculating a value of one or a plurality of the 9 formulae that include an explanatory variable to be substituted with a blood concentration value of at least one amino acid of the 17 kinds of amino acids, obtained from an animal, the value being calculated using the formula and the blood concentration value.

The present invention achieves the effect of being able to provide a person involved in an animal (for example, a livestock animal such as a pig) with sufficiently reliable information so that the person (for example, a farmer and an animal doctor when the animal is a livestock animal) can conveniently and objectively grasp any one or both of a health state and a growth state of the animal thereby contributing to realization of a rational rearing environment of the animal.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 5 is a drawing that illustrates an example of the information to be stored in a concentration data file 106a;

FIG. 6 is a drawing that illustrates an example of the information to be stored in an index state information file 106b;

FIG. 7 is a drawing that illustrates an example of the information to be stored in a specific index state information file 106c;

FIG. 8 is a drawing that illustrates an example of the information to be stored in a formula file 106d;

FIG. 9 is a drawing that illustrates an example of the information to be stored in a calculation result data file 106e;

FIG. 10 is a drawing that illustrates an example of the information to be stored in an evaluation result data file 106f;

FIG. 11 is a drawing that illustrates an example of the information to be stored in a recommendable amino acid data file 106g;

FIG. 12 is a drawing that illustrates an example of the information to be stored in an acquired result data file 106h;

FIG. 13 is a drawing that illustrates an example of the information to be stored in an ordering data file 106i;

FIG. 14 is a drawing that illustrates an example of the information to be stored in an opinion data file 106j;

FIG. 15 is a drawing that illustrates an example of a display mode of an evaluation result of an item;

FIG. 16 is a drawing that illustrates an example of a display mode of the evaluation result of the item;

FIG. 18 is a flow chart that illustrates an example of a processing that is carried out in the present system.

DETAILED DESCRIPTION OF THE PREFERRED EMBODIMENTS

Hereinafter, embodiments (first embodiment and second embodiment) of the present invention are described in detail with reference to the drawings. The present invention is not limited to these embodiments.

First Embodiment

Figure 1:
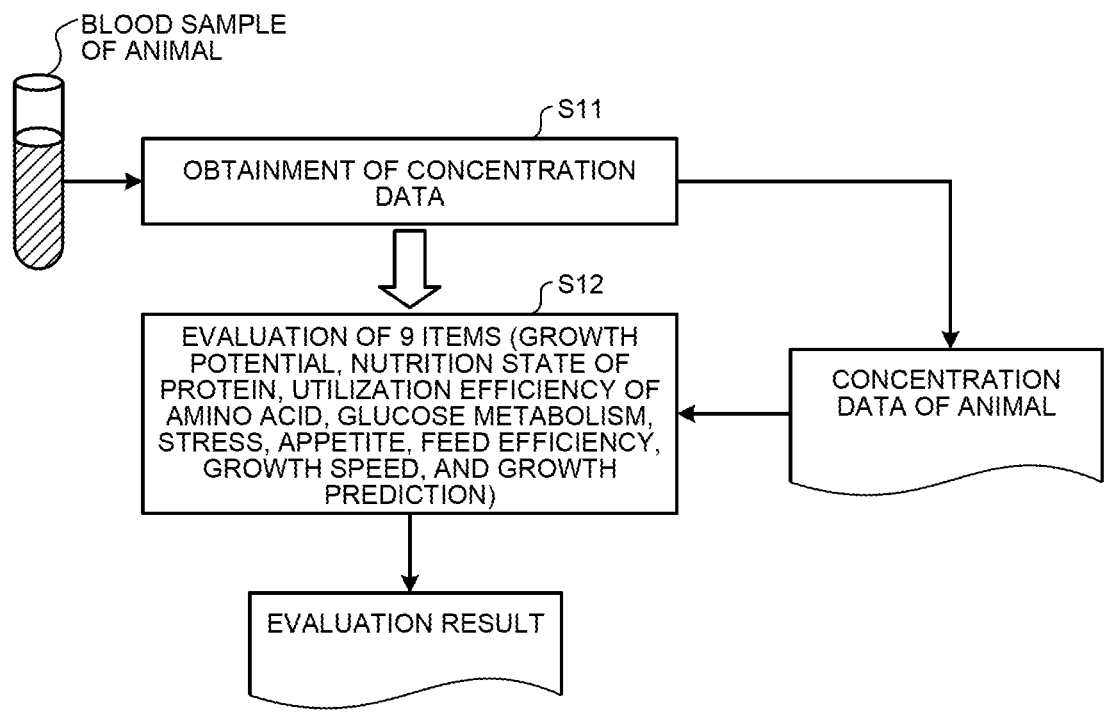
FIG. 1 is a drawing that shows an outline of a first embodiment.

Hereinafter, outlines of a first embodiment will be described with reference to FIG. 1. FIG. 1 is a drawing that shows the outline of the first embodiment.

Firstly, concentration data on a concentration value of at least one amino acid of the 17 kinds of amino acids in a blood (for example, a plasma or a serum) that is taken out from an animal (for example, a livestock animal such as a pig) except for human is obtained (Step S11). Here, the animal may be an animal that is reared in a specific rearing environment (for example, in a farm). When the animal is reared in the specific rearing environment and plural animals including this animal are reared in the specific rearing environment, the concentration values of these amino acids may be a represented value of these amino acids (average value, median value, or the like) that is calculated on the basis of plural concentration values of these amino acids obtained from plural animals arbitrarily selected from the plural animals (because these are the values reflecting the characteristics of the specific rearing environment such as a farm). In addition, the concentration values of these amino acids may be those in an artificial lactation period (specifically, those obtained from the animal in artificial lactation period). The concentration values of these amino acids may be of those with the daily age of 45 days to 60 days (specifically, those obtained from the animal with the daily age of 45 days to 60 days).

The concentration values may be, for example, those measured by a company or the like that carries out measurement of the concentration values. For example, the concentration values may be those obtained by a measuring method such as (A), (B), (C), or (D), as described below. The unit of the concentration value may be, for example, a molar concentration, a weight concentration, or an enzyme activity. They may be those obtained by adding, subtracting, multiplying, or dividing these concentrations with an arbitrary constant.

(A) A blood sample extracted is taken in a tube treated with EDTA-2Na, and then, this tube is centrifuged to separate a plasma from the blood. All the plasma samples are frozen and stored at −80° C. until the concentration value is measured. At the time of measuring the concentration value, after proteins are removed by adding thereto sulfosalicylic acid such that the concentration thereof may be adjusted at 3%, the concentration value is analyzed in a post-column by means of an amino acid analyzer based on a high-speed liquid chromatography (HPLC) using a ninhydrin reaction.

(B) A blood sample extracted is centrifuged to separate a plasma from the blood. All the plasma samples are frozen and stored at −80° C. until the concentration value is measured. At the time of measuring the concentration value, after proteins are removed by adding thereto sulfosalicylic acid, the concentration value is analyzed by means of an amino acid analyzer based on a post-column derivatization method using a ninhydrin reagent.

(C) A blood sample extracted is subjected to separation of blood cell by means of a membrane or a MEMS (Micro Electro Mechanical Systems) technology, or on the basis of a centrifugation principle, whereby a plasma or a serum is separated from the blood. The plasma sample or the serum sample that is not subjected to measurement of the concentration value immediately after the plasma or the serum is obtained is frozen and stored at −80° C. until the concentration value is measured. At the time of measuring the concentration value, by using a molecule such as an enzyme or an aptamer that can react with or bond to a target substance in the blood, the concentration value is analyzed by quantifying or the like a substance that can increase or decrease by substrate recognition or a spectroscopic value.

(D) A blood sample extracted is centrifuged to separate a plasma from the blood. The plasma sample or the serum sample that is not subjected to measurement of the concentration value immediately after the plasma or the serum is obtained is frozen and stored at −80° C. until the concentration value is measured. At the time of measuring the concentration value, the concentration value is analyzed by quantifying or the like by using various mass analysis technologies (mass spectrometry).

Next, by using the concentration value included in the concentration data obtained at step S11, at least one item of the 9 items is evaluated (step S12). Here, before executing the step S12, the data such as a missing value and an outlier may be removed from the concentration data obtained at step S11. At step S12, the evaluation may be carried out with regard to the animal, or when the animal is reared in the specific rearing environment, the evaluation may be carried out with regard to the specific rearing environment.

Consequently, according to the first embodiment, the concentration data are obtained; and by using the concentration value included in the concentration data thus obtained, at least one aforementioned item is evaluated. Through this, a person involved in an animal (for example, a livestock animal such as a pig) is provided with sufficiently reliable information so that the person (for example, a farmer and an animal doctor when the animal is a livestock animal) can conveniently and objectively grasp any one or both of a health state and a growth state of the animal thereby contributing to realization of a rational rearing environment of the animal.

When the growth potential is evaluated at step S12, the evaluation may be carried out by using the concentration value of at least one amino acid of Asn, Gly, Pro, Tyr, Lys, Ile, Leu, and Trp. When the nutrition state of a protein is evaluated at step S12, the evaluation may be carried out by using the concentration value of at least one amino acid of His, Arg, Tyr, Val, Lys, Ile, Leu, Phe, and Trp. When the utilization efficiency of an amino acid is evaluated at step S12, the evaluation may be carried out by using the concentration value of His. When the glucose metabolism is evaluated at step S12, the evaluation may be carried out by using the concentration value of at least one amino acid of Thr, Arg, Tyr, Met, Orn, and Phe. When the stress is evaluated at step S12, the evaluation may be carried out by using the concentration value of at least one amino acid of Ser, Tyr, Ile, and Trp. When the appetite is evaluated at step S12, the evaluation may be carried out by using the concentration value of Trp. When the feed efficiency is evaluated at step S12, the evaluation may be carried out by using the concentration value of 3Met-His. When the growth speed is evaluated at step S12, the evaluation may be carried out by using the concentration value of at least one amino acid of Pro, Tyr, Lys, Ile, Leu, and Trp. When the growth prediction is evaluated at step S12, the evaluation may be carried out by using the concentration value of at least one amino acid of Arg, Tyr, Ile, Phe, and Trp.

the concentration value of at least one amino acid of the 17 kinds of amino acids, or the value obtained by converting the concentration value by a converting method (the post-conversion value) such as the method described in the next paragraph may be used as the value that reflects the state of at least one item of the 9 items. In other words, the concentration value or the post-conversion value thereof may be used as the evaluation result of at least one item of the 9 items. For example, the concentration value of at least one amino acid of Asn, Gly, Pro, Tyr, Lys, Ile, Leu, and Trp, or the post-conversion value thereof may be used as the evaluation result of the growth potential. The concentration value of at least one amino acid of His, Arg, Tyr, Val, Lys, Ile, Leu, Phe, and Trp, or the post-conversion value thereof may be used as the evaluation result of the nutrition state of a protein. The concentration value of His or the post-conversion value thereof may be used as the evaluation result of the utilization efficiency of an amino acid. The concentration value of at least one amino acid of Thr, Arg, Tyr, Met, Orn, and Phe, or the post-conversion value thereof may be used as the evaluation result of the glucose metabolism. The concentration value of at least one amino acid of Ser, Tyr, Ile, and Trp, or the post-conversion value thereof may be used as the evaluation result of the stress. The concentration value of Trp or the post-conversion value thereof may be used as the evaluation result of the appetite. The concentration value of 3Met-His or the post-conversion value thereof may be used as the evaluation result of the feed efficiency. The concentration value of at least one amino acid of Pro, Tyr, Lys, Ile, Leu, and Trp, or the post-conversion value thereof may be used as the evaluation result of the growth speed. The concentration value of at least one amino acid of Arg, Tyr, Ile, Phe, and Trp, or the post-conversion value thereof may be used as the evaluation result of the growth prediction.

Examples of Converting Method

Example 11: For example, to bring the concentration value within an allowable predetermined range (for example, the range of 0.0 to 1.0, the range of 0.0 to 10.0, the range of 0.0 to 100.0, or the range of −10.0 to 10.0), the concentration value is converted by adding, subtracting, multiplying, or dividing with an arbitrary value, or by a prescribed converting method (for example, exponential conversion, logarithmic conversion, angular conversion, square root conversion, probit conversion, reciprocal conversion, Box-Cox conversion, or power conversion), or by combining these calculations to the concentration value. For example, the value of an exponential function with the concentration value as an exponent and the Napier's constant as an base may be calculated (specifically, the value of $p/(1-p)$ when a natural logarithm $\ln(p/(1-p))$ is equal to the concentration value, where the probability p under the state that the item is in a predetermined state is defined). Alternatively, the value (specifically, the value of the probability p) may be calculated by dividing a calculated value of the exponential function with the sum of 1 and this value.

Example 12: The concentration value is converted such that the post-conversion value may be a specific value under a specific condition. For example, the concentration value may be converted such that the post-conversion value may be 5.0 when the specificity is 80%, and that the post-conversion value may be 8.0 when the specificity is 95%.

Example 13: After normally distributing the concentration distribution in each amino acid, deviation values of the concentration values of each amino acid are calculated so as to give an average of 50 and a standard deviation of 10.

*Note: The conversions in Example 11 to Example 13 may be carried out in each of male and female, or in each monthly age.

At step S12, at least one item of the 9 items may be evaluated by calculating a value of one or a plurality of the 9 formulae that include an explanatory variable to be substituted with the concentration value of at least one amino acid of the 17 kinds of amino acids, the value being calculated using the formula and the concentration value. Here, the evaluation may be carried out with regard to the animal, or when the animal is reared in the specific rearing environment, the evaluation may be carried out with regard to the specific rearing environment.

Here, when the evaluation is carried out with regard to the growth potential at step S12, the evaluation may be carried out by calculating the value of the formula that includes the explanatory variable to be substituted with the concentration value of at least one amino acid of Asn, Gly, Pro, Tyr, Lys, Ile, Leu, and Trp, the value being calculated using the formula and the concentration value. When the evaluation is carried out with regard to the nutrition state of a protein at step S12, the evaluation may be carried out by calculating the value of the formula that includes the explanatory variable to be substituted with the concentration value of at least one amino acid of His, Arg, Tyr, Val, Lys, Ile, Leu, Phe, and Trp, the value being calculated using the formula and the concentration value. When the evaluation is carried out with regard to the utilization efficiency of an amino acid at step S12, the evaluation may be carried out by calculating the value of the formula that includes the explanatory variable to be substituted with the concentration value of His, the value being calculated using the formula and the concentration value. When the evaluation is carried out with regard to the glucose metabolism at step S12, the evaluation may be carried out by calculating the value of the formula that includes the explanatory variable to be substituted with the concentration value of at least one amino acid of Thr, Arg, Tyr, Met, Orn, and Phe, the value being calculated using the formula and the concentration value. When the evaluation is carried out with regard to the stress at step S12, the evaluation may be carried out by calculating the value of the formula that includes the explanatory variable to be substituted with the concentration value of at least one amino acid of Ser, Tyr, Ile, and Trp, the value being calculated using the formula and the concentration value. When the evaluation is carried out with regard to the appetite at step S12, the evaluation may be carried out by calculating the value of the formula that includes the explanatory variable to be substituted with the concentration value of Trp, the value being calculated using the formula and the concentration value. When the evaluation is carried out with regard to the feed efficiency at step S12, the evaluation may be carried out by calculating the value of the formula that includes the explanatory variable to be substituted with the concentration value of 3Met-His, the value being calculated using the formula and the concentration value. When the evaluation is carried out with regard to the growth speed at step S12, the evaluation may be carried out by calculating the value of the formula that includes the explanatory variable to be substituted with the concentration value of at least one amino acid of Pro, Tyr, Lys, Ile, Leu, and Trp, the value being calculated using the formula and the concentration value. When the evaluation is carried out with regard to the growth prediction at step S12, the evaluation may be carried out by calculating the value of the formula that includes the explanatory variable to be substituted with the concentration value of at least one amino acid of Arg, Tyr, Ile, Phe, and Trp, the value being calculated using the formula and the concentration value.

The value of the formula, or the value obtained by converting the value of the formula by a converting method (the post-conversion value) such as the method described in the next paragraph may be used as the value that reflects the state of at least one item of the 9 items. In other words, the value of the formula or the post-conversion value thereof may be used as the evaluation result of at least one item of the 9 items. For example, the value of the formula regarding the growth potential or the post-conversion value thereof may be used as the evaluation result of the growth potential. The value of the formula regarding the nutrition state of a protein or the post-conversion value thereof may be used as the evaluation result of the nutrition state of a protein. The value of the formula regarding the utilization efficiency of an amino acid or the post-conversion value thereof may be used as the evaluation result of the utilization efficiency of an amino acid. The value of the formula regarding the glucose metabolism or the post-conversion value thereof may be used as the evaluation result of the glucose metabolism. The value of the formula regarding the stress or the post-conversion value thereof may be used as the evaluation result of the stress. The value of the formula regarding the appetite or the post-conversion value thereof may be used as the evaluation result of the appetite. The value of the formula regarding the feed efficiency or the post-conversion value thereof may be used as the evaluation result of the feed efficiency. The value of the formula regarding the growth speed or the post-conversion value thereof may be used as the evaluation result of the growth speed. The value of the formula regarding the growth prediction or the post-conversion value thereof may be used as the evaluation result of the growth prediction.

Examples of Converting Method

Example 21: For example, to bring the value of the formula within an allowable predetermined range (for example, the range of 0.0 to 1.0, the range of 0.0 to 10.0, the range of 0.0 to 100.0, or the range of −10.0 to 10.0), the value of the formula is converted by adding, subtracting, multiplying, or dividing with an arbitrary value, or by a prescribed converting method (for example, exponential conversion, logarithmic conversion, angular conversion, square root conversion, probit conversion, reciprocal conversion, Box-Cox conversion, or power conversion), or by combining these calculations to the value of the formula. For example, the value of an exponential function with the value of the formula as an exponent and the Napier's constant as an base may be calculated (specifically, the value of $p/(1-p)$ when a natural logarithm $\ln(p/(1-p))$ is equal to the value of the formula, where the probability p under the state that the item is in a predetermined state is defined). Alternatively, the value (specifically, the value of the probability p) may be calculated by dividing a calculated value of the exponential function with the sum of 1 and this value.

Example 22: The value of the formula is converted such that the post-conversion value may be a specific value under a specific condition. For example, the value of the formula may be converted such that the post-conversion value may be 5.0 when the specificity is 80%, and that the post-conversion value may be 8.0 when the specificity is 95%.

Example 23: Deviation values of the values of the formula are calculated so as to give an average of 50 and a standard deviation of 10.

*Note: The conversions in Example 21 to Example 23 may be carried out in each of male and female, or in each monthly age.

At step S12, on the basis of the evaluation result of at least one item of the 9 items, at least one item of the 3 items may be further evaluated. For example, evaluation of the nutrition state may be carried out on the basis of the evaluation result of the growth potential and the evaluation result of the nutrition state of a protein; evaluation of the growth may be carried out on the basis of the evaluation result of the growth speed and the evaluation result of the growth prediction; and evaluation of the physiological response may be carried out on the basis of the evaluation result of the stress. Here, the evaluation may be carried out with regard to the animal, or when the animal is reared in the specific rearing environment, the evaluation may be carried out with regard to the specific environment.

The evaluation with regard to the item may be carried out qualitatively. Specifically, the evaluation result with regard to the item may be expressed by any one of plural classes (for example, "good", "not good", and "in-between", which will be described later). Specific examples of the evaluation method will be explained in detail in a second embodiment.

As for the formula used for the evaluation, the form of the formula is not specifically designated, however, for example, may be the following forms.

linear model such as multiple regression equation, linear discriminant, principal component analysis, and canonical discriminant analysis that are based on the least-squares method;

generalized linear model such as logistic regression and Cox regression that are based on the maximum likelihood method;

generalized linear mixed model considering random effects due to individual differences, facility differences, and other factors in addition to the generalized linear model expression generated by cluster analysis such as the K-means method and the hierarchical cluster analysis;

expression generated on the basis of the Bayesian statistics such as the Markov chain Monte Carlo (MCMC), the Bayesian network, and the hierarchical Bayesian method;

expression generated by class classification such as support vector machine and decision tree;

expression generated by a method that does not belong to the above-cited categories such as fractional expression; and expression represented as, example, the summation of expressions of different forms The formula used for the evaluation may be prepared by a method described in WO 2004/052191, which is incorporated herein by reference in its entirety, that is an international application filed by the present applicant or by a method described in WO 2006/098192, which is incorporated herein by reference in its entirety, that is an international application filed by the present applicant. Any formulae obtained by these methods can be preferably used in the evaluation of at least one item of the 9 items, regardless of the units of the concentrations of amino acids in the concentration data as input data.

In the multiple regression equation, the multiple logistic regression equation, and the canonical discriminant function, a coefficient and a constant term are added to each explanatory variable, and the coefficient and the constant term may be preferably real numbers, more preferably values in the range of 99% confidence interval for the coefficient and the constant term obtained from data for various kinds of evaluations, more preferably values in the range of 95% confidence interval for the coefficient and the constant term obtained from data for various kinds of evaluations. The value of each coefficient and the confidence interval thereof may be those multiplied by a real number, and the value of the constant term and the confidence interval thereof may be those having an arbitrary actual constant added or subtracted or those multiplied or divided by an arbitrary actual constant. When an expression such as the logistic regression, the linear discriminant, and the multiple regression equation is used for the evaluation, a linear transformation of the expression (addition of a constant and multiplication by a constant) and a monotonic increasing (decreasing) transformation (for example, a logit transformation) of the expression do not alter evaluation performance and thus evaluation performance after transformation is equivalent to that before transformation. Therefore, the expression includes an expression that is subjected to the linear transformation and the monotonic increasing (decreasing) transformation.

In the fractional expression, the numerator of the fractional expression is expressed by the sum of the explanatory variables A, B, C etc. and the denominator of the fractional expression is expressed by the sum of the explanatory variables a, b, c etc. The fractional expression also includes the sum of the fractional expressions $\alpha$, $\beta$, $\gamma$ etc. (for example, $\alpha+\beta$) having such constitution. The fractional expression also includes divided fractional expressions. The explanatory variables used in the numerator or denominator may have suitable coefficients respectively. The explanatory variables used in the numerator or denominator may appear repeatedly. Each fractional expression may have a suitable coefficient. A value of a coefficient for each explanatory variable and a value for a constant term may be any real numbers. In a fractional expression and the one in which explanatory variables in the numerator and explanatory variables in the denominator in the fractional expression are switched with each other, the positive and negative signs are generally reversed in correlation with objective explanatory variables, but because their correlation is maintained, the evaluation performance can be assumed to be equivalent. The fractional expression therefore also includes the one in which explanatory variables in the numerator and explanatory variables in the denominator in the fractional expression are switched with each other.

Second Embodiment

2-1. Outline of Second Embodiment

Figure 2:
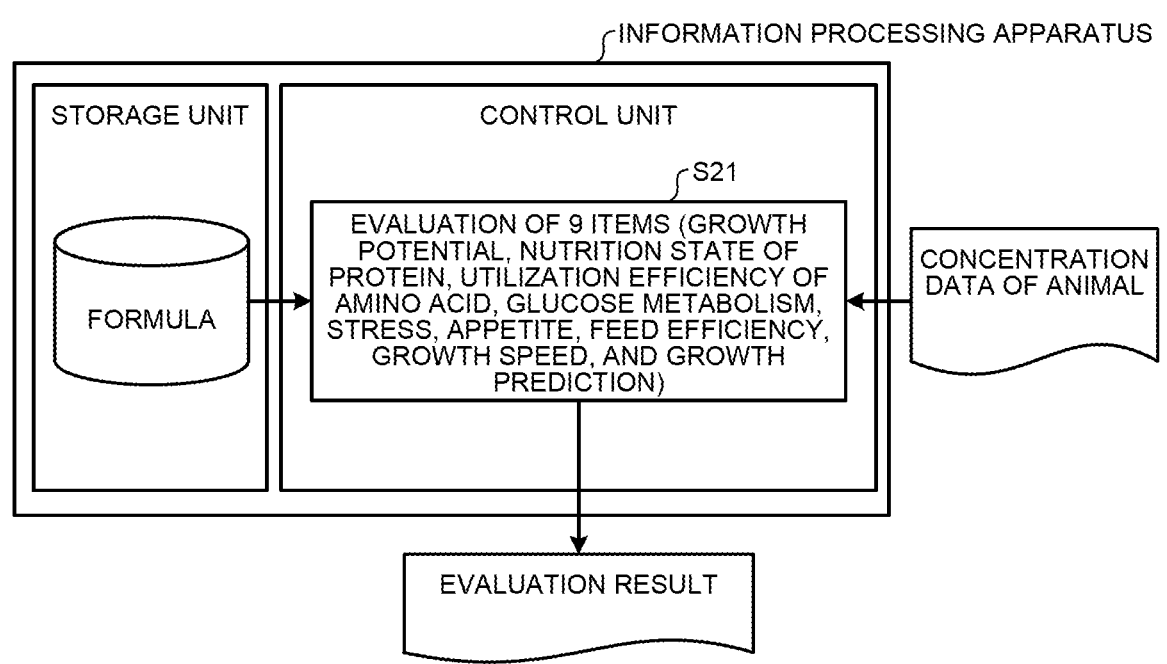
FIG. 2 is a drawing that shows an outline of a second embodiment.

Hereinafter, outlines of a second embodiment will be described with reference to FIG. 2. FIG. 2 is a principle configurational diagram that illustrates a basic principle of the second embodiment. In the description of the second embodiment, a description duplicating that of the first embodiment is sometimes omitted. Especially here, at the time of evaluating the item, an example is described that the value of the formula or the post-conversion value thereof is used; for example, the concentration value of at least one amino acid of the 17 kinds of amino acids or the post-conversion value thereof (for example, concentration deviation value) may be used.

A control unit evaluates at least one item of the 9 items by calculating the value of one or a plurality of the 9 formulae that are previously stored in a storage unit and include the explanatory variable to be substituted with the concentration value of at least one amino acid of the 17 kinds of amino acids included in the previously obtained concentration data, the value being calculated using the formula and the concentration value (step S21). Through this, the person involved in the animal (for example, a livestock animal such as a pig) is provided with sufficiently reliable information so that the person (for example, a farmer and an animal doctor when the animal is a livestock animal) can conveniently and objectively grasp any one or both of a health state and a growth state of the animal thereby contributing to realization of a rational rearing environment of the animal.

At step S21, on the basis of the evaluation result of at least one item of the 9 items, the control unit may further evaluate at least one item of the 3 items. For example, the control unit may carry out evaluation of the nutrition state on the basis of the evaluation result of the growth potential and the evaluation result of the nutrition state of a protein. For example, the control unit may carry out evaluation of the growth on the basis of the evaluation result of the growth speed and the evaluation result of the growth prediction. For example, the control unit may carry out evaluation of the physiological response on the basis of the evaluation result of the stress.

At step S21, the control unit may carry out the evaluation with regard to the animal, or when the animal is reared in the specific rearing environment, may carry out the evaluation with regard to the specific environment.

The control unit may set, item by item, any one or both of a color and a pattern corresponding to the evaluation result of the item obtained at step S21, and prepare the result data with regard to a tile display of a rectangular area of each item in which any one or both of the color and the pattern in the area are those having been set and in which a character string corresponding to the respective items is disposed in the area. Alternatively, the control unit may prepare the result data with regard to the evaluation result of the item, the result having been obtained at step S21 and being displayed in a table style or in a list style.

In addition, from recommendable amino acid data including a recommendable amino acid in each item and having been previously stored in the storage unit, the amino acid being recommended to improve evaluation result of the item (for example, the data includes, as the recommendable amino acid, at least one amino acid of Met, Lys, Thr, Trp, Val, Leu, Ile, Arg, Tyr, Phe, Gln, Glu, Gly, Cys2, and His), the control unit may acquire the recommendable amino acid corresponding to the item that is resulted in a unfavorable evaluation at step S21.

In addition, the control unit may prepare ordering data of the recommendable amino acid thus obtained and may transmit the ordering data thus prepared to an information processing apparatus of a company that sells amino acids, the information processing apparatus being communicably connected to this apparatus through a network.

In addition, on the basis of the evaluation results of the items obtained at step S21, the control unit may prepare opinion data (for example, text data, voice data, or video data) to improve a rearing condition of an animal.

In addition, the control unit may transmit the result data, the recommendable amino acids obtained, and the opinion data to an information processing apparatus of a receiver (for example, a framer) that receives the service through this apparatus.

The formula used at step S21 may be generated based on the formula-preparing processing (step 1 to step 4) described below. Here, the summary of the formula-preparing processing is described. The processing described below is merely one example, and the method of preparing the formula is not limited thereto.

First, the control unit prepares a candidate formula (e.g., $y=a_1x_1+a_2x_2+ \ldots +a_nx_n$, y: index data, $x_i$: concentration data, $a_i$: constant, i=1, 2, . . . , n) based on a predetermined formula-preparing method from index state information data that are previously stored in the storage unit and include the concentration data and index data on an index representing a state of the item (the data such as a missing value and an outlier may be removed from the index state information in advance) (step 1).

When preparing the formula to evaluate the growth potential, the index data may be of the blood IGF-1 concentration value, which is the indicator of the growth potential. When preparing the formula to evaluate the nutrition state of a protein, the index data may be of the blood albumin concentration value, which is the indicator of the nutrition state of a protein. When preparing the formula to evaluate the utilization efficiency of an amino acid, the index data may be of the blood 3Met-His concentration value, which is the indicator of the utilization efficiency of an amino acid.

When preparing the formula to evaluate the glucose metabolism, the index data may be of the blood insulin concentration value, which is the indicator of the glucose metabolism. When preparing the formula to evaluate the stress, the index data may be of the Trp/Kyn ratio, which is the index of the stress (see Gislaine Z. Reus, Karen Jansen, Stephanie Titus, Andre F. Carvalho, Vilma Gabbay, Joao Quevedo; Kynurenine pathway dysfunction in the pathophysiology and treatment of depression: evidences from animal and human studies; J. Psychiatr. Res., 2015 September; 68: 316-328, which is incorporated herein by reference in its entirety). When preparing the formula to evaluate the appetite, the index data may be of ADFI (Average Daily Feed Intake), which is the index of the appetite.

When preparing the formula to evaluate the feed efficiency, the index data may be of G:F (Gain to Feed Ratio), which is the index of the feed efficiency. When preparing the formula to evaluate the growth speed, the index data may be of "change amount of body length from a weaning period to an artificial lactation period" ($\Delta$ body length), which is the index of the growth speed. When preparing the formula to evaluate the growth prediction, the index data may be of the body weight in a late stage of rearing (late rearing body weight), which is the indicator of the growth prediction.

In step 1, a plurality of the candidate formulae may be prepared from the index state information by using a plurality of the different formula-preparing methods (including those for multivariate analysis such as principal component analysis, discriminant analysis, support vector machine, multiple regression analysis, Cox regression analysis, logistic regression analysis, K-means method, cluster analysis, and decision tree). Specifically, a plurality of groups of the candidate formulae may be prepared simultaneously and concurrently by using a plurality of different algorithms with the index state information which is multivariate data composed of the concentration data and the index data obtained by analyzing blood obtained from a large number of individuals. For example, the two different candidate formulae may be formed by performing discriminant analysis and logistic regression analysis simultaneously with the different algorithms. Alternatively, the candidate formula may be formed by converting the index state information with the candidate formula prepared by performing principal component analysis and then performing discriminant analysis of the converted index state information. In this way, it is possible to finally prepare the most suitable formula for the evaluation.

The candidate formula prepared by the principal component analysis is a linear expression including each explanatory variable maximizing the variance of all concentration data. The candidate formula prepared by the discriminant analysis is a high-powered expression (including exponential and logarithmic expressions) including each explanatory variable minimizing the ratio of the sum of the variances in respective groups to the variance of all concentration data. The candidate formula prepared by using the support vector machine is a high-powered expression (including kernel function) including each explanatory variable maximizing the boundary between groups. The candidate formula prepared by using the multiple regression analysis is a high-powered expression including each explanatory variable minimizing the sum of the distances from all concentration data. The candidate formula prepared by using the Cox regression analysis is a linear model including a logarithmic hazard ratio, and is a linear expression including each explanatory variable with a coefficient thereof maximizing the likelihood of the linear model. The candidate formula prepared by using the logistic regression analysis is a linear model expressing logarithmic odds of probability, and a linear expression including each explanatory variable maximizing the likelihood of the probability. The K-means method is a method of searching k pieces of neighboring concentration data in various groups, designating the group containing the greatest number of the neighboring points as its data-belonging group, and selecting the explanatory variable that makes the group to which input concentration data belong agree well with the designated group. The cluster analysis is a method of clustering (grouping) the points closest in entire concentration data. The decision tree is a method of ordering explanatory variables and predicting the group of concentration data from the pattern possibly held by the higher-ordered explanatory variable.

Returning to the description of the formula-preparing processing, the control unit verifies (mutually verifies) the candidate formula prepared in step 1 based on a particular verifying method (step 2). The verification of the candidate formula is performed on each other to each candidate formula prepared in step 1. In step 2, at least one of discrimination rate, sensitivity, specificity, information criterion, and ROC_AUC (area under the curve in a receiver operating characteristic curve) of the candidate formula may be verified by at least one of bootstrap method, holdout method, N-fold method, and leave-one-out method. In this way, it is possible to prepare the candidate formula having high predictability or high reliability, in which the index state information and the evaluation condition are taken into consideration.

The discrimination rate is a rate in which, by the evaluating method according to this embodiment, a subject to be evaluated (animal or rearing environment) whose true state is negative is correctly evaluated as negative, and a subject to be evaluated whose true state is positive is correctly evaluated as positive. The sensitivity is a rate in which by the evaluation method according to the present embodiment, a subject to be evaluated whose true state is positive is correctly evaluated as positive. The specificity is a rate in which by the evaluation method according to the present embodiment, a subject to be evaluated whose true state is negative is correctly evaluated as negative. The Akaike information criterion is a criterion representing how observation data agrees with a statistical model; for example, in the regression analysis, this judges that the model in which the value defined by "$-2\times$(maximum log-likelihood of statistical model)$+2\times$(the number of free parameters of statistical model)" is smallest is the best. ROC_AUC is defined as the area under the receiver operating characteristics curve (ROC) created by plotting $(x, y)=(1\text{-specificity, sensitivity})$ on two-dimensional coordinates. The value of ROC_AUC is 1 in perfect discrimination, and the closer this value is to 1, the higher the discriminative characteristic is. The predictability is the average of discrimination rates, sensitivities, or specificities obtained by repeating the validation of the candidate formula. The robustness is the variance of discrimination rates, sensitivities, or specificities obtained by repeating the validation of the candidate formula.

Returning to the description of the formula-preparing processing, the control unit selects a combination of the concentration data included in the index state information used in preparing the candidate formula, by selecting an explanatory variable of the candidate formula based on a predetermined explanatory variable-selecting method (step 3). In step 3, the selection of the explanatory variable may be performed on each candidate formula prepared in step 1. In this way, it is possible to select the explanatory variable of the candidate formula properly. The step 1 is executed once again by using the index state information including the concentration data selected in step 3. In step 3, the explanatory variable of the candidate formula may be selected based on at least one of stepwise method, best path method, local search method, and genetic algorithm from the verification result obtained in step 2. The best path method is a method of selecting an explanatory variable by optimizing an evaluation index of the candidate formula while eliminating the explanatory variables contained in the candidate formula one by one.

Returning to the description of the formula-preparing processing, the control unit prepares the formula used for the evaluation by repeatedly performing steps 1, 2 and 3, and based on the verification results thus accumulated, selecting the candidate formula used for the evaluation from the candidate formulae (step 4). In the selection of the candidate formula, there are cases where the optimum formula is selected from the candidate formulae prepared in the same formula-preparing method or the optimum formula is selected from all candidate formulae.

As described above, in the formula-preparing processing, the processing for the preparation of the candidate formulae, the verification of the candidate formulae, and the selection of the explanatory variables in the candidate formulae are performed based on the index state information in a series of operations in a systematized manner, whereby the formula most appropriate for evaluating the item can be prepared. In other words, in the formula-preparing processing, the concentration values of amino acids are used in multivariate statistical analysis, and for selecting the optimum and robust combination of the explanatory variables, the explanatory variable-selecting method is combined with cross-validation to extract the formula having high evaluation performance.

2-2. Configuration

Hereinafter, configurations of the information processing system according to the second embodiment (hereinafter referred to sometimes as the present system) will be described with reference to FIGS. 3 to 17. This system is merely one example, and the present invention is not limited thereto. Especially here, at the time of evaluating the item, an example is described that the value of the formula or the post-conversion value thereof is used; for example, the concentration value of at least one amino acid of the 17 kinds of amino acids or the post-conversion value thereof (for example, concentration deviation value) may be used.

Figure 3:
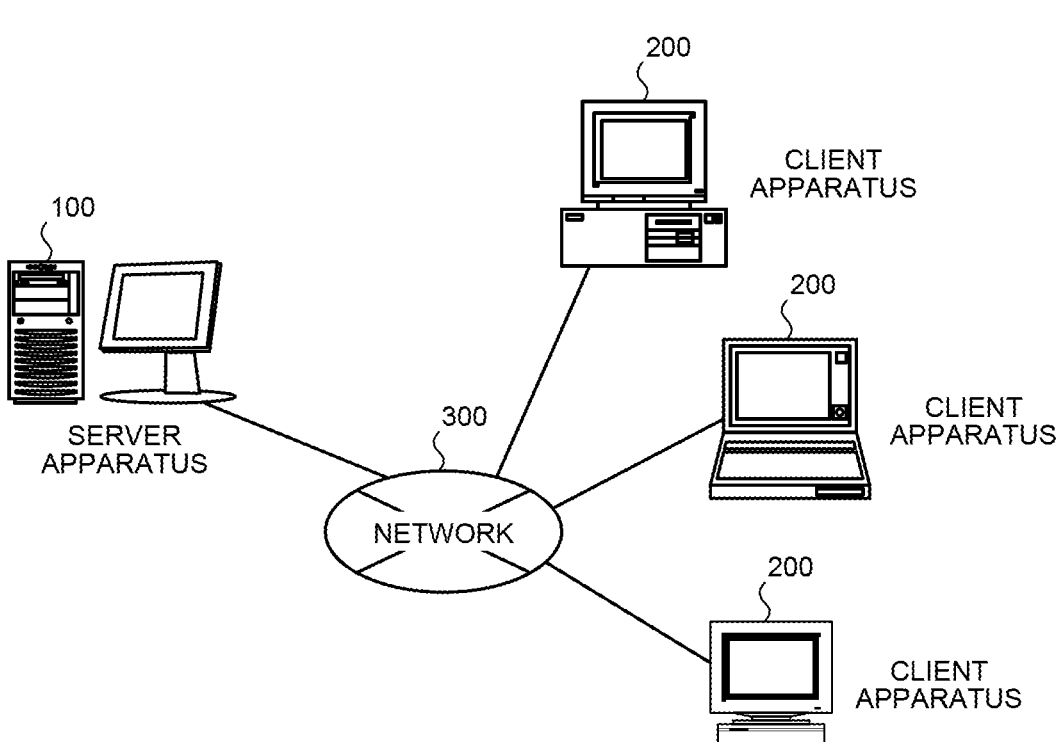
FIG. 3 is a drawing that illustrates an example of an entire configuration of a present system.

First, an entire configuration of the present system will be described with reference to FIG. 3. FIG. 3 is a drawing that illustrates an example of the entire configuration of the present system. The present system includes the server apparatus 100 to provide a service, the client apparatus 200 of a receiver of the service (for example, a farmer), and a network 300 (for example, an internet). The server apparatus 100 and the client apparatus 200 are communicatively connected to each other via the network 300. Illustrative examples of the client apparatus 200 include a stationary personal computer, a mobile personal computer, and a smartphone. The present system may further include the client apparatus 200 of a company that carries out concentration measurement of an amino acid, the client apparatus 200 of a company that sells an amino acid, and the like.

Figure 4:
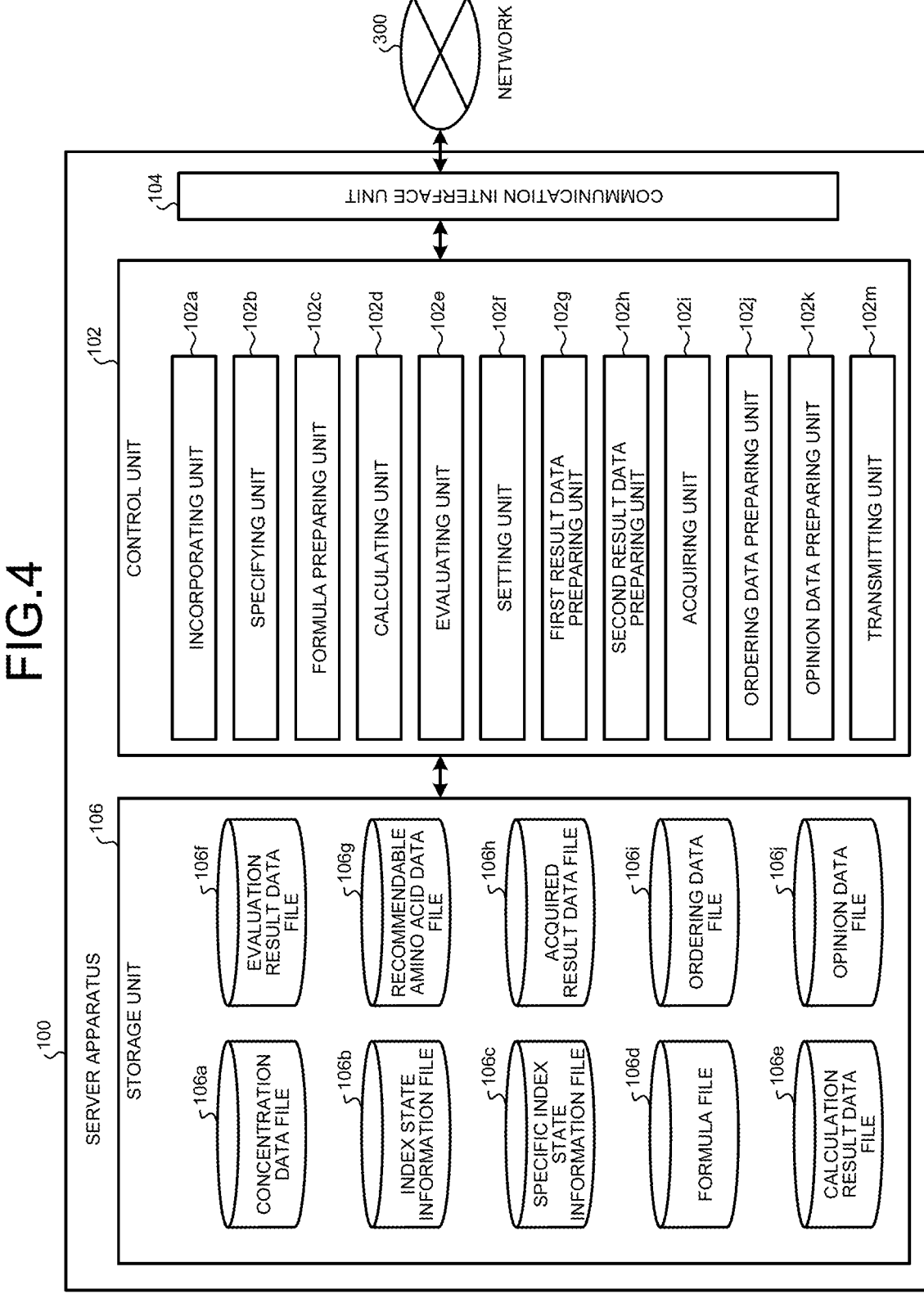
FIG. 4 is a block diagram that illustrates an example of a configuration of a server apparatus 100.

Now, the configuration of the server apparatus 100 will be described with reference to FIGS. 4 to 16. FIG. 4 is a block diagram that illustrates an example of the configuration of the server apparatus 100, illustrating conceptually only the region relevant to the present invention.

The server apparatus 100 includes a control unit 102, such as CPU (Central Processing Unit), that integrally controls the server apparatus, a communication interface 104 that connects the server apparatus to the network 300 communicatively via communication apparatuses such as a router and wired or wireless communication lines such as a private line, and a storage unit 106 that stores various databases, tables, files and others.

The communication interface 104 allows communication between the server apparatus 100 and the network 300 (or a communication apparatus such as a router). Thus, the communication interface 104 has a function to communicate data via a communication line with other terminals.

The storage unit 106 is a storage means, and examples thereof include a memory apparatus such as RAM (Random Access Memory) and ROM (Read Only Memory), a fixed disk drive such as a hard disk, a flexible disk, and an optical disk. The storage unit 106 stores computer programs giving instructions to the CPU for various processings, together with OS (Operating System).

The storage unit 106 stores the concentration data file 106a, the index state information file 106b, the specific index state information file 106c, the formula file 106d, the calculation result data file 106e, the evaluation result data file 106f, the recommendable amino acid data file 106g, the acquired result data file 106h, the ordering data file 106i, and the opinion data file 106j.

FIG. 5 is a drawing that illustrates an example of the information to be stored in the concentration data file 106a. The concentration data file 106a stores the concentration data of the concentration value of at least one amino acid of the 17 kinds of amino acids. The concentration data file 106a may store, for example, the individual identification information to uniquely identify the animal, the environment identification information to uniquely identify the rearing environment, and the customer identification information to uniquely identify the receiver of the service, in which each of information is correlated with the concentration data.

FIG. 6 is a drawing that illustrates an example of the information to be stored in the index state information file 106b. The index state information file 106b stores the index state information to be used for preparation of each of the 9 formulae. The index state information file 106b may store, for example, the individual identification information, the concentration data, the index data with regard to the indexes indicating the state of each of the 9 items (specifically, the blood IGF-1 concentration value, which is the indicator of the growth potential; the blood albumin concentration value, which is the indicator of the nutrition state of a protein; the blood 3Met-His concentration value, which is the indicator of the utilization efficiency of an amino acid, the blood insulin concentration value, which is the indicator of the glucose metabolism, the Trp/Kyn ratio which is the index of the stress; ADFI which is the index of the appetite; G:F which is the index of the feed efficiency; the Δ body length which is the index of the growth speed; and the late rearing body weight which is the indicator of the growth prediction).

FIG. 7 is a drawing that illustrates an example of the information to be stored in the specific index state information file 106c. The specific index state information file 106c stores the specific index state information that is specified in the specifying unit 102b to be described later. The specific index state information file 106c may store, for example, the individual identification information, the specified concentration data, and the specified index data.

FIG. 8 is a drawing that illustrates an example of the information to be stored in the formula file 106d. The formula file 106d stores the formulae to be used (specifically, the 9 formulae, and the like) upon evaluating the items, the formulae having been prepared in the formula preparing unit 102c to be described later. The formula file 106d may store, for example, rank, formula, threshold value corresponding to preparation method of each formula, and inspection result of each formula (for example, value of each formula), in which these are correlated with the item identification information to uniquely identify the item.

FIG. 9 is a drawing that illustrates an example of the information to be stored in the calculation result data file 106e. The calculation result data file 106e stores the values of the formulae corresponding to each of the 9 formulae, the values having been calculated in the calculating unit 102d to be described later. The calculation result data file 106e may store, for example, the individual identification information, the environment identification information, and the customer identification information, in which each of the information is correlated with the values of the formulae.

FIG. 10 is a drawing that illustrates an example of the information to be stored in the evaluation result data file 106f. The evaluation result data file 106f stores the evaluation results (for example, any one of "good", "not good", and "in-between", to be described later) of each of the 9 items as well as the evaluation results of each of the 3 items (for example, any one of "good", "not good", and "in-between", to be discussed later), these evaluation results having been obtained in the evaluating unit 102e to be described later. The evaluation result data file 106f may store, for example, the individual identification information, the environment identification information, and the customer identification information, in which each of the information is correlated with the evaluation results. The evaluation result data file 106f may further store, as the evaluation results, the result data that are prepared in the first result data preparing unit 102g and the result data that are prepared in the second result data preparing unit 102h, these units to be described later.

FIG. 11 is a drawing that illustrates an example of the information to be stored in the recommendable amino acid data file 106g. The recommendable amino acid data file 106g stores the recommendable amino acids that improve the evaluation results corresponding to each item (for example, "not good" to be described later), in which the recommendable amino acids are correlated with the item identification information.

As for the recommendable amino acid corresponding to the growth potential, it is preferable to use an amino acid that can contribute to retention and improvement of a digestive tract function. Illustrative examples of the amino acid that can contribute to retention and improvement of the digestive tract function include BCAA (Val, Leu, and Ile), Arg, Glu, and Gln (the reason for this is as described below), which have the action of retaining and improving the digestive tract function.

BCAA contributes to retention of a digestive tract shape owing to the facilitation action of synthesis of a protein to be described later. It is reported that Arg not only contributes to retention of the digestive tract shape (see reference 1 described below) but also have the action of reducing migration of a microorganism in a body (see reference 2 described below). It is reported that Glu and Gln are one of the major energy sources of intestinal tract cells (see reference 3 described below). From these reports, it is presumed that BCAA and Arg retain the structures of the digestive tracts thereby retaining and improving the barrier function of the digestive tracts, and that Glu and Gln retain the action level of the digestive tract cells as the energy substrates thereof thereby retaining and improving the digestive absorption function of the digestive tracts.

Reference 1: K. Yao, S. Guan, T. J. Li, R. L. Huang, G. Y. Wu, Z. Ruan, Y. L. Yin, "Dietary L-arginine supplementation enhances intestinal development and expression of vascular endothelial growth factor in weanling piglets," British Journal of Nutrition, 2011, which is incorporated herein by reference in its entirety.

Reference 2: B. Zulfikaroglu, E. Zulfikaroglu, M. M. Ozmen, N. Ozalp, R. Berkem, S. Erdogan, H. T. Besler, M. Koc, A. Korkmaz, "The effect of immunonutrition on bacterial translocation, and intestinal villus atrophy in experimental obstructive jaundice," Clinical Nutrition, 2003, which is incorporated herein by reference in its entirety.

Reference 3: Guoyao Wu, Fuller W. Bazer, Teresa A. Davis, Sung Woo Kim, Peng Li, J. Marc Rhoads, M. Carey Satterfield, Stephen B. Smith, Thomas E. Spencer, and Yulong Yin, "Arginine metabolism and nutrition in growth, health and disease", Amino Acids. 2009 May; 37(1): 153-168, which is incorporated herein by reference in its entirety.

It is preferable to use, as the recommendable amino acid corresponding to the nutrition state of a protein, an amino acid that can contribute to retention and improvement of the digestive tract function and an amino acid that can contribute to suppression of decomposition and facilitation of synthesis of a protein. Illustrative examples of the amino acid that can contribute to suppression of decomposition and facilitation of synthesis of a protein include BCAA, which has the action of suppressing decomposition and facilitation of synthesis of a protein (the reason for this is as described below).

BCAA is a nitrogen source in the syntheses of Gln and Ala. It has been known that when the amino acid concentrations in BCAA in a muscle are increased, decomposition of a protein is suppressed (see reference 4 described below). In a pig, too, among BCAA, especially Leu expresses the action of suppressing decomposition and facilitation of synthesis of a protein through mTOR (mammalian target of rapamycin) (see reference 5 described below), but addition of only Leu to a feed does not improve an increase in the body weight thereof (see references 6 and 7 described below); and thus, it is preferable to use BCAA.

Reference 4: M. Holecek, "Relation between glutamine, branched-chain amino acids, and protein metabolism," Nutrition, 2002, which is incorporated herein by reference in its entirety.

Reference 5: R. Murgas Torrazza, A. Suryawan, M. C. Gazzaneo, R. A. Orellana, J. W. Frank, H. V. Nguyen, M. L. Fiorotto, S. El-Kadi, T. A. Davis, "Leucine Supplementation of a Low-Protein Meal Increases Skeletal Muscle and Visceral Tissue Protein Synthesis in Neonatal Pigs by Stimulating mTOR-Dependent Translation Initiation," Journal of Nutrition, 2010, which is incorporated herein by reference in its entirety.

Reference 6: M. S. Edmonds, D. H. Baker, "Amino acid excesses for young pigs: effects of excess methionine, tryptophan, threonine or leucine," Journal of animal science, 1987, which is incorporated herein by reference in its entirety.

Reference 7: C. J. Lynch, B. J. Patson, Anthony, A. Vaval, L. S. Jefferson, T. C. Vary, "Leucine is a direct-acting nutrient signal that regulates protein synthesis in adipose tissue," American journal of physiology. Endocrinology and metabolism, 2002, which is incorporated herein by reference in its entirety.

It is preferable to use, as the recommendable amino acid corresponding to the utilization efficiency of an amino acid, an amino acid that can contribute to suppression of decomposition and facilitation of synthesis of a protein. It is preferable to use, as the recommendable amino acid corresponding to the glucose metabolism, an amino acid that can contribute to retention and improvement of the digestive tract function.

It is preferable to use, as the recommendable amino acid corresponding to the stress, an amino acid that can contribute to relaxation of an inflammatory response and an amino acid that can contribute to relaxation of a stress response. Illustrative examples of the amino acid that can contribute to relaxation of the inflammatory response include Trp, Phe, and Tyr, which have an action of relaxing the inflammatory response (the reason for this is as described below). Illustrative examples of the amino acid that can contribute to relaxation of the stress response include Trp, which has an action of relaxing the stress response (the reason for this is as described below).

The amino acid sidechains of the proteins such as CRP (c-reactive protein) and AGP (α1-acid glycoprotein), which relate to an inflammatory disease, are rich in Trp, Phe, and Tyr, so that it is presumed that the requirement amounts of these amino acids increase at the time of response to the inflammatory disease (see reference 8 described below). It is also reported that the inflammatory response can be relaxed by addition of Trp to a pig feed (see reference 9 described below). Because of these, Trp, Phe, and Tyr can contribute to productivity improvement of a pig by relaxation of the inflammatory response and by satisfying the requirement amount at the time of response to the inflammatory disease.

It is reported that addition of Trp to a feed can reduce saliva and a stress hormone in a blood (see references 10, 11, and 12 described below).

Reference 8: N. Le Floc'h, D. Melchior, C. Obled, "Modifications of protein and amino acid metabolism during inflammation and immune system activation," Livestock Production Science, 2004, which is incorporated herein by reference in its entirety.

Reference 9: N. Le Floc'h, D. Melchior, B. Seve, "Dietary tryptophan helps to preserve tryptophan homeostasis in pigs suffering from lung inflammation," Journal of Animal Science, 2008, which is incorporated herein by reference in its entirety.

Reference 10: S. J. Koopmans, A. C. Guzik, J. Van Der Meulen, R. Dekker, J. Kogut, B. J. Kerr, L. L. Southern, "Effects of supplemental L-tryptophan on serotonin, cortisol, intestinal integrity, and behavior in weanling piglets," Journal of Animal Science, 2006, which is incorporated herein by reference in its entirety.

Reference 11: Y. B. Shen, G. Voilque, J. Odle, S. W. Kim, "Dietary L-Tryptophan Supplementation with Reduced Large Neutral Amino Acids Enhances Feed Efficiency and Decreases Stress Hormone Secretion in Nursery Pigs under Social-Mixing Stress," Journal of Nutrition, 2012, which is incorporated herein by reference in its entirety.

Reference 12: Gislaine Z. Reus, Karen Jansen, Stephanie Titus, Andre F. Carvalho, Vilma Gabbay, Joao Quevedo, "Kynurenine pathway dysfunction in the pathophysiology and treatment of depression: evidences from animal and human studies", J Psychiatr Res. 2015 September; 68: 316-328, which is incorporated herein by reference in its entirety.

It is preferable to use, as the recommendable amino acid corresponding to the appetite, an amino acid that can contribute to relaxation of the stress response and an amino acid that can contribute to relaxation of the inflammatory response. It is preferable to use, as the recommendable amino acid corresponding to the feed efficiency, an amino acid that can contribute to retention and improvement of the digestive tract function, an amino acid that can contribute to relaxation of the stress response, and an amino acid that can contribute to relaxation of the inflammatory response.

It is preferable to use, as the recommendable amino acid corresponding to the growth speed, an amino acid that can contribute to retention and improvement of the digestive tract function, an amino acid that can contribute to suppression of decomposition and facilitation of synthesis of a protein, an amino acid that can contribute to relaxation of the stress response, and an amino acid that can contribute to relaxation of the inflammatory response. It is preferable to use, as the recommendable amino acid corresponding to the growth prediction, an amino acid that can contribute to retention and improvement of the digestive tract function, an amino acid that can contribute to suppression of decomposition and facilitation of synthesis of a protein, an amino acid that can contribute to relaxation of the stress response, and an amino acid that can contribute to relaxation of the inflammatory response.

In order to improve an amino acid balance in a feed thereby improving the evaluation results of each of the 9 items, restriction amino acids such as Lys (see reference 13 described below), Met (see reference 14 described below), Thr (see reference 15 described below), Gly (see reference 16 described below), Cyst (see reference 17 described below), and His (see reference 17 described below) may be added as the recommendable amino acid of each item.

Reference 13: E. T. Kornegay, M. D. Lindemann, V. Ravindran, "Effects of dietary lysine levels on performance and immune response of weanling pigs housed at two floor space allowances," Journal of animal science, 1993, which is incorporated herein by reference in its entirety.

Reference 14: Y. B. Shen, A. C. Weaver, S. W. Kim, "Effect of feed grade L-methionine on growth performance and gut health in nursery pigs compared with conventional DL-methionine," Journal of Animal Science, 2014, which is incorporated herein by reference in its entirety.

Reference 15: D. F. Li, C. T. Xiao, S. Y. Qiao, J. H. Zhang, E. W. Johnson, P. A. Thacker, "Effects of dietary threonine on performance, plasma parameters and immune function of growing pigs," Animal Feed Science and Technology, 1999, which is incorporated herein by reference in its entirety.

Reference 16: W. Wang, Z. Dai, Z. Wu, G. Lin, S. Jia, S. Hu, S. Dahanayaka, G. Wu, "Glycine is a nutritionally essential amino acid for maximal growth of milk-fed young pigs," Amino Acids, 2014, which is incorporated herein by reference in its entirety.

Reference 17: Jean-Paul LALLES, Gaelle BOUDRY, Christine FAVIER, Nathalie LE FLOC'Ha, Isabelle LURONa, Lucile MONTAGNE, Isabelle P. OSWALD, Sandrine PIE, Christelle PIEL, Bernard SEVE, "Gut function and dysfunction in young pigs:physiology", Anim. Res., 2004, which is incorporated herein by reference in its entirety.

It is preferable to use, as the recommendable amino acid corresponding to the nutrition state, the recommendable amino acid corresponding to the growth potential and the recommendable amino acid corresponding to the nutrition state of a protein. It is preferable to use, as the recommendable amino acid corresponding to the growth, the recommendable amino acid corresponding to the growth speed and the recommendable amino acid corresponding to the growth prediction. It is preferable to use, as the recommendable amino acid corresponding to the physiological response, the recommendable amino acid corresponding to the stress.

FIG. 12 is a drawing that illustrates an example of the information to be stored in the acquired result data file 106h. The acquired result data file 106h stores the recommendable amino acids that are acquired in the acquiring unit 102i to be described later. The acquired result data file 106h may store, for example, the individual identification information, the environment identification information, and the customer identification information, in which each of the information is correlated with the recommendable amino acids.

FIG. 13 is a drawing that illustrates an example of the information to be stored in the ordering data file 106i. The ordering data file 106i stores the ordering data that are prepared in the ordering data preparing unit 102j to be described later. The ordering data file 106i may store, for example, the customer identification information and the ordering destination identification information to uniquely identify the ordering destination, in which each of the information is correlated with the ordering data.

FIG. 14 is a drawing that illustrates an example of the information to be stored in the opinion data file 106j. The opinion data file 106j stores the opinion data that are prepared in the opinion data preparing unit 102k to be described later. The opinion data file 106j may store, for example, the individual identification information, the environment identification information, and the customer identification information, in which each of the information is correlated with the opinion data.

Returning to FIG. 4, the control unit 102 has an internal memory storing, for example, control programs such as OS (Operating System), programs for various processing procedures, and other needed data, and performs various information processings according to these programs.

The control unit 102 includes functionally and conceptually an incorporating unit 102a, the specifying unit 102b, the formula preparing unit 102c, the calculating unit 102d, the evaluating unit 102e, a setting unit 102f, the first result data preparing unit 102g, the second result data preparing unit 102h, the acquiring unit 102i, the ordering data preparing unit 102j, the opinion data preparing unit 102k, and a transmitting unit 102m.

The incorporating unit 102a incorporates information (for example, concentration data and index state information). The incorporating unit 102a may incorporate concentration data by receiving the concentration data, which are sent through the network 300 from the client apparatus 200 of a company that measures the concentration value of an amino acid, and which can be correlated with the receiver of the service. When the server apparatus 100 has a mechanism (including a hardware and a software) to read out the data that are recorded in a recording medium, the incorporating unit 102a may incorporate the concentration data that are read out by the mechanism from the recording medium, in which the concentration data that can be correlated with the receiver of the service are written. In addition, the incorporating unit 102a may store the incorporated concentration data in the concentration data file 106a. The incorporating unit 102a may also store the incorporated index state information in the index state information file 106b.

At the time of preparing the formula, the specifying unit 102b specifies the target concentration data and index data from the index state information stored in the index state information file 106b. Here, the specifying unit 102b may store the specified concentration data and index data in the specific index state information file 106c.

The formula preparing unit 102c prepares the formula on the basis of the index state information that is incorporated by the incorporating unit 102a or of the index state information that is specified by the specifying unit 102b. Here, when the formula is previously stored in a predetermined storage area of the storage unit 106, the formula preparing unit 102c may prepare the formula by selecting an intended formula from the storage unit 106. Alternatively, the formula preparing unit 102c may prepare the formula by selecting and downloading the intended formula from other computer that previously stored the formulae. The formula preparing unit 102c may store the prepared formula in the formula file 106d.

The calculating unit 102d calculates the value of one or a plurality of the 9 formulae that include the explanatory variable to be substituted with the concentration value of at least one amino acid of the 17 kinds of amino acids, the value being calculated using the formula and the concentration value.

The calculating unit 102d may calculate the value of the formula for evaluating the growth potential that includes the explanatory variable to be substituted with the concentration value of at least one amino acid of Asn, Gly, Pro, Tyr, Lys, Ile, Leu, and Trp, the value being calculated using the formula and the concentration value. The calculating unit 102d may calculate the value of the formula for evaluating the nutrition state of a protein that includes the explanatory variable to be substituted with the concentration value of at least one amino acid of His, Arg, Tyr, Val, Lys, Ile, Leu, Phe, and Trp, the value being calculated using the formula and the concentration value. The calculating unit 102d may calculate the value of the formula for evaluating the utilization efficiency of an amino acid that includes the explanatory variable to be substituted with the concentration value of His, the value being calculated using the formula and the concentration value. The calculating unit 102d may calculate the value of the formula for evaluating the glucose metabolism that includes the explanatory variable to be substituted with the concentration value of at least one amino acid of Thr, Arg, Tyr, Met, Orn, and Phe, the value being calculated using the formula and the concentration value. The calculating unit 102d may calculate the value of the formula for evaluating the stress that includes the explanatory variable to be substituted with the concentration value of at least one amino acid of Ser, Tyr, Ile, and Trp, the value being calculated using the formula and the concentration value. The calculating unit 102d may calculate the value of the formula for evaluating the appetite that includes the explanatory variable to be substituted with the concentration value of Trp, the value being calculated using the formula and the concentration value. The calculating unit 102d may calculate the value of the formula for evaluating the feed efficiency that includes the explanatory variable to be substituted with the concentration value of 3Met-His, the value being calculated using the formula and the concentration value. The calculating unit 102d may calculate the value of the formula for evaluating the growth speed that includes the explanatory variable to be substituted with the concentration value of at least one amino acid of Pro, Tyr, Lys, Ile, Leu, and Trp, the value being calculated using the formula and the concentration value. The calculating unit 102d may calculate the value of the formula for evaluating the growth prediction that includes the explanatory variable to be substituted with the concentration value of at least one amino acid of Arg, Tyr, Ile, Phe, and Trp, the value being calculated using the formula and the concentration value.

The evaluating unit 102e carries out evaluation of at least one item of the 9 items with regard to the animal or the rearing environment, using the value of the formula calculated by the calculating unit 102d. The evaluating unit 102e may store the evaluation result in the evaluation result data file 106f. On the basis of the evaluation result of at least one item of the 9 items, the evaluating unit 102e may further carry out evaluation of at least one item of the 3 items with regard to the animal or the rearing environment. For example, the evaluating unit 102e may carry out evaluation of the nutrition state on the basis of the evaluation result of the growth potential and the evaluation result of the nutrition state of a protein; may carry out evaluation of the growth on the basis of the evaluation result of the growth speed and the evaluation result of the growth prediction; and may carry out evaluation of the physiological response on the basis of the evaluation result of the stress.

The setting unit 102f sets, item by item, any one or both of a color and a pattern corresponding to the evaluation result obtained by the evaluating unit 102e. The setting unit 102f may set, for example, any one or both of the color and the pattern corresponding to the evaluation result of each of the 9 items obtained by the evaluating unit 102e. The setting unit 102f may set, for example, any one or both of the color and the pattern corresponding to the evaluation result of each of the 3 items obtained by the evaluating unit 102e.

Figure 15:
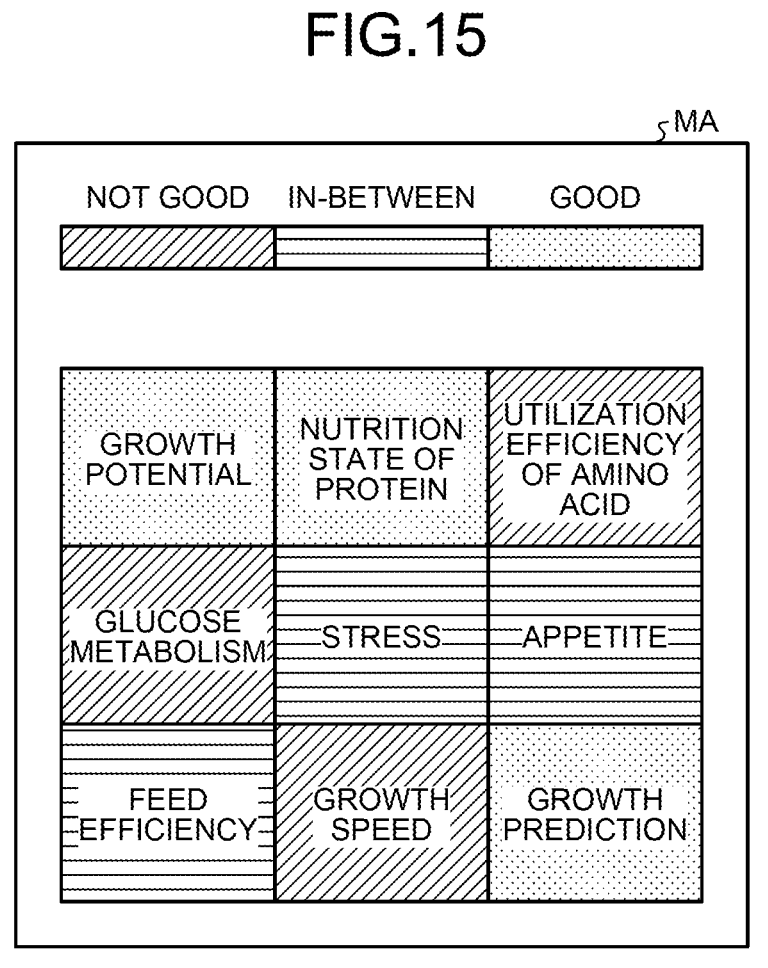

The first result data preparing unit 102g prepares the result data with regard to a tile display of a rectangular area (tile) of each item in which any one or both of the color and the pattern in the area are those having been set in the setting unit 102f and in which a character string corresponding to the respective items is disposed in the area. The first result data preparing unit 102g may store the result data thus prepared in the evaluation result data file 106f. Here, an example of the tile display is illustrated in FIG. 15. FIG. 15 illustrates an example of the tile display of the 9 rectangular areas corresponding to the 9 items; but the number of the rectangular area displayed is not limited to the number in this example. The tile display directing to the 3 items may be similar to that in the example illustrated in FIG. 15.

The second result data preparing unit 102h prepares the result data with regard to the evaluation results of the items displayed in a table style or in a list style and obtained by the evaluating unit 102e. The second result data preparing unit 102h may store the result data thus prepared in the evaluation result data file 106f. Here, an example of the display in the table style or in the list style is illustrated in FIG. 16. FIG. 16 illustrates an example that displays the evaluation results of each of the 9 items; but the number of the displaying items is not limited to the number in this example. The display directing to the 3 items may be similar to that in the example illustrated in FIG. 16.

The acquiring unit 102i acquires, from the recommendable amino acid data file 106g, the recommendable amino acid corresponding to the item whose evaluation result obtained in the evaluating unit 102e is unfavorable (for example, the evaluation result of "not good" to be described later). The acquiring unit 102i may store the recommendable amino acid thus acquired in the acquired result data file 106h.

The ordering data preparing unit 102j prepares the ordering data (the data including an ordering date, an ordering good, an ordering number, a desirable manufacturer, and the like) of the recommendable amino acid acquired in the acquiring unit 102i. The ordering data preparing unit 102j may store the ordering data thus prepared in the ordering data file 106i.

The opinion data preparing unit 102k prepares, on the basis of the evaluation results obtained in the evaluating unit 102e, the opinion data (for example, text data) with regard to improvement of the rearing condition of an animal. The opinion data preparing unit 102k may store the opinion data thus prepared in the opinion data file 106j.

The transmitting unit 102m transmits the information (for example, the result data, the acquired recommendable amino acid, the ordering data, and the opinion data). The transmitting unit 102m may transmit, for example, the result data, the acquired recommendable amino acid, and the opinion data to the client apparatus 200 of the receiver of the service. The transmitting unit 102m may transmit, for example, the ordering data to the client apparatus 200 of the company that sells the amino acid.

Figure 17:
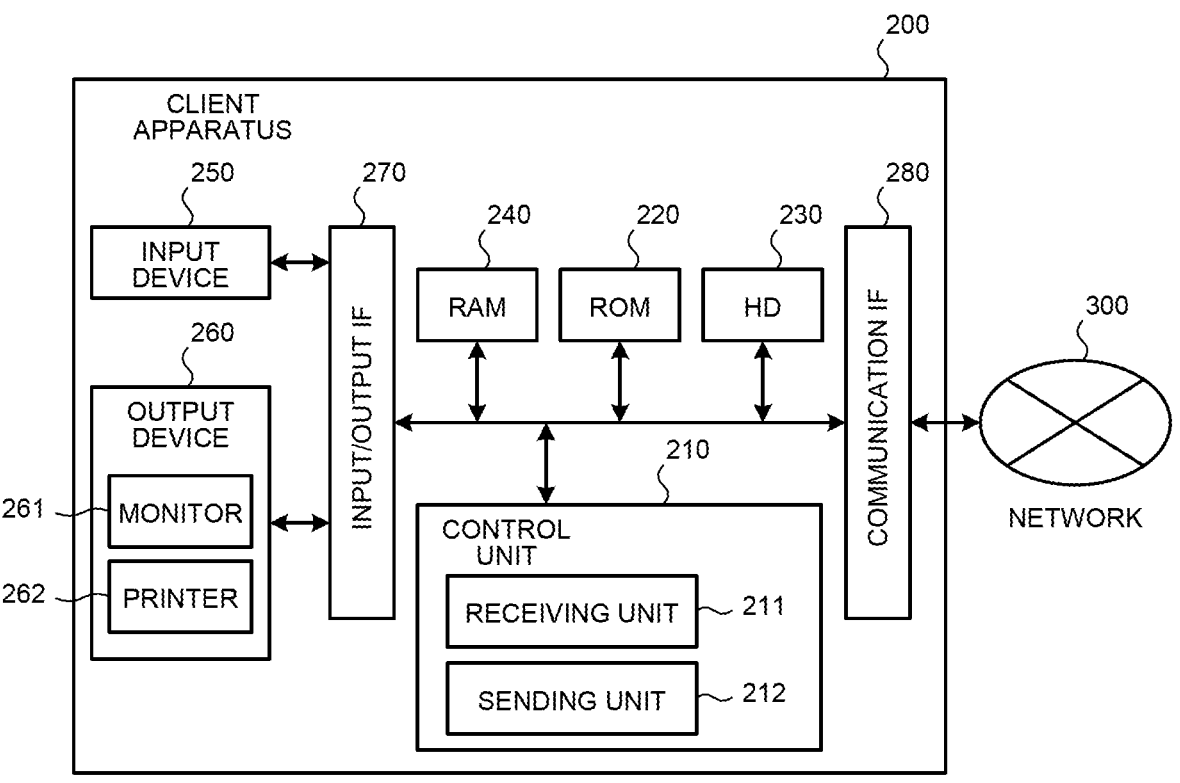
FIG. 17 is a block diagram that illustrates an example of a configuration of a client apparatus 200.

Hereinafter, a configuration of the client apparatus 200 will be described with reference to FIG. 17. FIG. 17 is a block diagram that illustrates an example of the configuration of the client apparatus 200, and only the part in the configuration relevant to the present invention is illustrated conceptually. The configuration of the client apparatus 200 assumes a general personal computer.

The client apparatus 200 includes a control unit 210, ROM 220, HD (Hard Disk) 230, RAM 240, an input device 250, an output device 260, an input/output IF 270, and a communication IF 280 that are connected communicatively to one another through a communication channel.

The input device 250 is, for example, a keyboard, a mouse, or a microphone. A monitor 261 described below also realizes a pointing device function together with a mouse. The output device 260 is an output means for outputting information received via the communication IF 280, and includes the monitor 261 (including home television) and a printer 262. In addition, the output device 260 may have a speaker or the like additionally. The input/output IF 270 is connected to the input device 250 and the output device 260.

The communication IF 280 connects the client apparatus 200 to the network 300 (or communication apparatus such as a router) communicatively. In other words, the client apparatus 200 is connected to the network 300 via a communication apparatus such as a modem, TA (Terminal Adapter) or a router, and a telephone line, or via a private line. In this way, the client apparatus 200 can access to the server apparatus 100 using a particular protocol.

The control unit 210 has an internal memory storing, for example, control programs such as OS, programs for various processing procedures, and other needed data, and performs various information processings according to these programs. The control unit 210 has a receiving unit 211 and a sending unit 212. The receiving unit 211 receives information (for example, the result data, the recommendable amino acid acquired, the ordering data, and the opinion data) transmitted from the server apparatus 100, via the communication IF 280. The sending unit 212 sends information (for example, the concentration data), via the communication IF 280, to, for example, the server apparatus 100.

2-3. Processing

Hereinafter, an example of the processing that is carried out in the present system will be described with reference to FIG. 18. FIG. 18 is a flow chart that illustrates an example of the processing that is carried out in the present system.

Step SA1: Incorporation of Concentration Data

The incorporating unit 102a incorporates the concentration data by receiving through the network 300 the concentration data that are linked to a farmer (hereinafter, "farmer X") who receives the service that is transmitted from the client apparatus 200 of a company that measures a concentration value of an amino acid. Here, the concentration data thus incorporated include blood concentration values of the 17 kinds of amino acids obtained from the blood of one pig (hereinafter, "individual A") that is reared in a farm of the farmer X (hereinafter, this farm is described as "farm Y").

Step SA2: Calculation of Values of Formulae

The calculating unit 102d calculates the values of formulae with regard to the individual A on the basis of the concentration data that are incorporated at step SA1 as well as the formula for evaluation of the growth potential, the formula for evaluation of the nutrition state of a protein, the formula for evaluation of the utilization efficiency of an amino acid, the formula for evaluation of the glucose metabolism, the formula for evaluation of the stress, the formula for evaluation of the appetite, the formula for evaluation of the feed efficiency, the formula for evaluation of the growth speed, and the formula for evaluation of the growth prediction.

The formula for evaluation of the growth potential may be a formula such as, for example, a multiple regression equation (one or more explanatory variables) in which a blood concentration value of an amino acid having a correlation with a blood IGF-1 concentration value is an explanatory variable and the blood IGF-1 concentration value is an objective variable. Here, as the explanatory variable, an amino acid such as Asn, Gly, Pro, Tyr, Lys, Ile, Leu, or Trp, which are described in Example 1 below, may also be used. In addition, as the formula for evaluation of the growth potential, a formula such as the index formula 1, which is described in Example 2 below, may also be used.

The formula for evaluation of the nutrition state of a protein may be a formula such as, for example, a multiple regression equation (one or more explanatory variables) in which a blood concentration value of an amino acid having a correlation with a blood albumin concentration value is an explanatory variable and the blood albumin concentration value is an objective variable. Here, as the explanatory variable, an amino acid such as His, Arg, Tyr, Val, Lys, Ile, Leu, Phe, or Trp, which are described in Example 1 below, may also be used. In addition, as the formula for evaluation of the nutrition of a protein, a formula such as the index formula 2, which is described in Example 2 below, may also be used.

The formula for evaluation of the utilization efficiency of an amino acid may be a formula such as, for example, a multiple regression equation (one or more explanatory variables) in which a blood concentration value of an amino acid (except for 3Met-His) having a correlation with a blood 3Met-His concentration value is an explanatory variable and the blood 3Met-His concentration value is an objective variable. Here, as the explanatory variable, an amino acid such as His, which is described in Example 1 below, may also be used. In addition, as the formula for evaluation of the utilization efficiency of an amino acid, a formula such as the index formula 3, which is described in Example 2 below, may also be used.

The formula for evaluation of the glucose metabolism may be a formula such as, for example, a multiple regression equation (one or more explanatory variables) in which a blood concentration value of an amino acid having a correlation with a blood insulin concentration value is an explanatory variable and the blood insulin concentration value is an objective variable. Here, as the explanatory variable, an amino acid such as Thr, Arg, Tyr, Met, Orn, or Phe, which are described in Example 1 below, may also be used. In addition, as the formula for evaluation of the glucose metabolism, a formula such as the index formula 4, which is described in Example 2 below, may also be used.

The formula for evaluation of the stress may be a formula such as, for example, a multiple regression equation (one or more explanatory variables) in which a blood concentration value of an amino acid having a correlation with the Trp/Kyn ratio is an explanatory variable and the Trp/Kyn ratio is an objective variable. Here, as the explanatory variable, an amino acid such as Ser, Tyr, Ile, or Trp, which are described in Example 1 below, may also be used. In addition, as the formula for evaluation of the stress, a formula such as the index formula 5, which is described in Example 2 below, may also be used.

The formula for evaluation of the appetite may be a formula such as, for example, a multiple regression equation (one or more explanatory variables) in which a blood concentration value of an amino acid having a correlation with ADFI is an explanatory variable and ADFI is an objective variable. Here, as the explanatory variable, an amino acid such as Trp, which is described in Example 1 below, may also be used. In addition, as the formula for evaluation of the appetite, a formula such as the index formula 6, which is described in Example 2 below, may also be used.

The formula for evaluation of the feed efficiency may be a formula such as, for example, a multiple regression equation (one or more explanatory variables) in which a blood concentration value of an amino acid having a correlation with G:F is an explanatory variable and G:F is an objective variable. Here, as the explanatory variable, an amino acid such as 3Met-His, which is described in Example 1 below, may also be used. In addition, as the formula for evaluation of the feed efficiency, a formula such as the index formula 7, which is described in Example 2 below, may also be used.

The formula for evaluation of the growth speed may be a formula such as, for example, a multiple regression equation (one or more explanatory variables) in which a blood concentration value of an amino acid having a correlation with the Δ body length is an explanatory variable and the Δ body length is an objective variable. Here, as the explanatory variable, an amino acid such as Pro, Tyr, Lys, Ile, Leu, or Trp, which are described in Example 1 below, may also be used. In addition, as the formula for evaluation of the growth speed, a formula such as the index formula 8, which is described in Example 2 below, may also be used.

The formula for evaluation of the growth prediction may be a formula such as, for example, a multiple regression equation (one or more explanatory variables) in which a blood concentration value of an amino acid having a correlation with the late rearing body weight is an explanatory variable and the late rearing body weight is an objective variable. Here, as the explanatory variable, an amino acid such as Arg, Tyr, Ile, Phe, or Trp, which are described in Example 1 below, may also be used. In addition, as the formula for evaluation of the growth prediction, a formula such as the index formula 9, which is described in Example 2 below, may also be used.

Step SA3: Item Evaluation

Next, on the basis of the value of each formula with regard to the individual A calculated at step SA2 (hereinafter, this value is described as "calculated value"), the evaluating unit 102e evaluates the state of the farm Y with regard to each of the 9 items.

Specifically, on the basis of the calculated value of the individual A obtained by the formula for evaluation of the growth potential, the evaluating unit 102e evaluates the farm Y with regard to the growth potential. On the basis of the calculated value of the individual A obtained by the formula for evaluation of the nutrition state of a protein, the evaluating unit 102e evaluates the farm Y with regard to the nutrition state of a protein. On the basis of the calculated value of the individual A obtained by the formula for evaluation of the utilization efficiency of an amino acid, the evaluating unit 102e evaluates the farm Y with regard to the utilization efficiency of an amino acid.

On the basis of the calculated value of the individual A obtained by the formula for evaluation of the glucose metabolism, the evaluating unit 102e evaluates the farm Y with regard to the glucose metabolism. On the basis of the calculated value of the individual A obtained by the formula for evaluation of the stress, the evaluating unit 102e evaluates the farm Y with regard to the stress. On the basis of the calculated value of the individual A obtained by the formula for evaluation of the appetite, the evaluating unit 102e evaluates the farm Y with regard to the appetite.

On the basis of the calculated value of the individual A obtained by the formula for evaluation of the feed efficiency, the evaluating unit 102e evaluates the farm Y with regard to the feed efficiency. On the basis of the calculated value of the individual A obtained by the formula for evaluation of the growth speed, the evaluating unit 102e evaluates the farm Y with regard to the growth speed. On the basis of the calculated value of the individual A obtained by the formula for evaluation of the growth prediction, the evaluating unit 102e evaluates the farm Y with regard to the growth prediction.

At step SA3, evaluation of the farm Y with regard to each of the 9 items may be carried out by any of the evaluation methods 1 to 3 described below.

Evaluation Method 1: Evaluation Based on Normalized Value

By carrying out the processes of the following steps 11 to 13, evaluation of the farm Y with regard to the item is carried out.

Step 11: On the basis of the calculated values aggregation composed of the calculated value of the individual A and the plural values calculated in the past (for example, those stored in the calculated result data file 106e) with regard to the pigs that are reared in each of plural farms, each of the calculated values are normalized by prescribed plural normalization methods. Through this, the normalized value of each of the calculated values that is normalized by each of the normalization methods can be obtained (hereinafter this value is described as "normalized value"). Here, the normalization method may be, for example, a method in which the value is converted so as to give the distribution having the average of 0 and the dispersion of 1 (z-score normalization method), or a method in which the value is converted so as to give the distribution having the minimum value of 0 and the maximum value of 1 (min-max normalization method).

Step 12: On the basis of the normalized values aggregation (including the normalized value of the individual A) composed of plural normalized values corresponding to one normalizing method, the normalized value of the individual A is confirmed in this normalized values aggregation whether this belongs to the group of upper 20%, or belongs to the group of upper 80% and does not belong to the upper 20%, or belongs to the group of lower 20%. The same confirmation is carried out with regard to the plural normalized values (including the normalized value of the individual A) corresponding to the rest of the normalization method.

Step 13: When all the normalized values of the individual A are confirmed to belong to the upper 20%, the state of the farm Y with regard to the item is evaluated as "good"$_{*1}$, when at least one normalized value of the individual A is confirmed to belong to the lower 20%$_{*2}$, the state of the farm Y with regard to the item is evaluated as "not good"$_{*1}$, and in the rest of the cases$_{*3}$, the state of the farm Y with regard to the item is evaluated as "in-between"$_{*1}$.

*1: Expressions of "good", "not good", and "in-between" are only an example. This means that when the normalized value is higher, the item is better; and thus, keeping this in mind, suitable expression may be used. For example, the expression like "relatively high", "relatively low", and "standard", the expression like "relatively good", "relatively bad", and "fair", the expression like "three stars", "two stars", and "one star", the expression like "gold", "silver", and "copper", the expression like "green sign", "yellow sign", and "red sign", and the like may be used.
*2: For example, when all the normalized values of the individual A are confirmed to belong to the lower 20%.
*3: For example, when all the normalized values of the individual A are confirmed to belong to the upper 80% and not to belong to the upper 20%.

The steps 12 and 13 may be displaced by the steps 14 and 15 described below.

Step 14: The normalized value of the individual A corresponding to one normalization method is compared with, for example, the previously set two cut-off values A and B (A<B) having different sensitivities (for example, 80% and 40%); and then, the normalized value of the individual A is confirmed whether this is equal to or more than the cut-off value B, whether this is equal to or more than the cut-off value A and less than the cut-off value B, and whether this is less than the cut-off value A. The same confirmation is carried out with regard to the normalized value of the individual A corresponding to the rest of the normalization methods.

Step 15: When all the normalized values of the individual A are confirmed to be equal to or more than the cut-off value B, the state of the farm Y with regard to the item is evaluated as "good"; when at least one normalized value of the individual A is confirmed to be less than the cut-off value A (for example, when all the normalized values of the individual A are confirmed to be less than the cut-off value A), the state of the farm Y with regard to the item is evaluated as "not good"; and in the rest of the cases (for example, when all the normalized values of the individual are confirmed to be equal to or more than the cut-off value A and less than the cut-off value B), the state of the farm Y with regard to the item is evaluated as "in-between".

The normalized value of the individual A may be output as the evaluation result.

Evaluation Method 2: Evaluation Based on the ABC Method

By carrying out the processes of the following steps 21 to 22, evaluation of the farm Y with regard to the item is carried out.

Step 21: On the basis of the calculated value of the individual A and the calculated values aggregation composed of the plural values calculated in the past (for example, those stored in the calculated result data file 106*e*) with regard to the pigs that are reared in each of plural farms, the cumulative rate of the calculated value of the individual A is calculated. Here, the cumulative rate of the calculated value of the individual A is the one obtained by calculation of the equation, [sum of the values from the maximum calculated value till the calculated value of the individual A when all of the calculated values of the calculated values aggregation are arranged in descending order]÷[sum of the total calculated values]×100. In this calculation, when the calculated value of the individual A is the maximum calculated value, the sum is equal to the calculated value of the individual A.

Step 22: When the cumulative rate is 80% or less, the state of the farm Y with regard to the item is evaluated as "good"; when the cumulative rate is more than 80% and 95% or less, the state of the farm Y with regard to the item is evaluated as "in-between"; and when the cumulative rate is more than 95%, the state of the farm Y with regard to the item is evaluated as "not good".

The step 22 may be displaced by the step 23 described below.

Step 23: The cumulative rate is compared with, for example, the previously set two cut-off values A and B (A<B) having different sensitivities (for example, 80% and 40%); and when the cumulative rate is equal to or more than the cut-off value B, the state of the farm Y with regard to the item is evaluated as "good"; when the cumulative rate is equal to or more than the cut-off value A and less than the cut-off value B, the state of the farm Y with regard to the item is evaluated as "in-between"; and when the cumulative rate is less than the cut-off value A, the state of the farm Y with regard to the item is evaluated as "not good".

The cumulative rate with regard to the calculated value of the individual A may be output as the evaluation result.
Evaluation Method 3: Evaluation Based on the Value Converted by Exponential Function By carrying out the processes of the following steps 31 to 33, evaluation of the farm Y with regard to the item is carried out.

Step 31: Each of the calculated value of the individual A and plural values calculated in the past (for example, those stored in the calculated result data file 106*e*) with regard to the pigs that are reared in each of plural farms is converted by calculating the formula $[1÷(1+Exp(-calculated\ value))]$. With this, the converted value of each of the calculated values can be obtained (hereinafter, this value is described as "converted value").

Step 32: On the basis of the converted values aggregation (including the converted value of the individual A) composed of the plural converted values, in the converted values aggregation, confirmation is made whether the converted value of the individual A belongs to the upper 20%, or belongs to the upper 80% and does not belong to the upper 20%, or belongs to the lower 20%.

Step 33: When it is confirmed that the converted value of the individual A belongs to upper 20%, the state of the farm Y with regard to the item is evaluated as "good"; when it is confirmed that the converted value of the individual A belongs to lower 20%, the state of the farm Y with regard to the item is evaluated as "not good"; and when it is confirmed that the converted value of the individual A belongs to upper 80% and does not belong to the upper 20%, the state of the farm Y with regard to the item is evaluated as "in-between".

The steps 32 and 33 may be displaced by the step 34 described below.

Step 34: The converted value of the individual A is compared with, for example, the previously set two cut-off values A and B (A<B) having different sensitivities (for example, 80% and 40%); and when the converted value is equal to or more than the cut-off value B, the state of the farm Y with regard to the item is evaluated as "good"; when the converted value is equal to or more than the cut-off value A and less than the cut-off value B, the state of the farm Y with regard to the item is evaluated as "in-between"; and when the converted value is less than the cut-off value A, the state of the farm Y with regard to the item is evaluated as "not good".

The converted value of the individual A may be output as the evaluation result.

Explanation of the evaluation methods 1 to 3 is over here.

At step SA3, the farm Y may be further evaluated with regard to each of the 3 items.

Specifically, in accordance with a combination of the evaluation result of the growth potential and the evaluation result of the nutrition state of a protein, the nutrition state of the farm Y may be evaluated. More specifically, when the combination of the evaluation results is of "good" and "good", the nutrition state of the farm Y may be evaluated as "good"; when at least one "not good" is included in the combination of the evaluation results, the nutrition state of the farm Y may be evaluated as "not good"; and when the combination of the evaluation results is other than the above, the nutrition state of the farm Y may be evaluated as "in-between".

Also, specifically, in accordance with a combination of the evaluation result of the growth speed and the evaluation result of the growth prediction, the growth in the farm Y may be evaluated. More specifically, when the combination of the evaluation results is of "good" and "good", the growth in the farm Y may be evaluated as "good"; when at least one "not good" is included in the combination of the evaluation results, the growth in the farm Y may be evaluated as "not good"; and when the combination of the evaluation results is other than the above, the growth in the farm Y may be evaluated as "in-between".

Also, specifically, the physiological response of the farm Y may be evaluated on the basis of the evaluation result of the stress. More specifically, when the evaluation result thereof is "good", the physiological response of the farm Y may be evaluated as "good"; when the evaluation result thereof is "not good", the physiological response of the farm Y may be evaluated as "not good"; when the evaluation result thereof is "in-between", the physiological response of the farm Y may be evaluated as "in-between".
Step SA4: Preparation of Tile Display Data The setting unit 102*f* sets to the farm Y, on the basis of the content of the evaluation results that are obtained at step SA3, the color corresponding to the evaluation result of each of the 9 items. Specifically, the setting unit 102*f* sets a blue color when the evaluation result is "good", a yellow color is set when the evaluation result is "in-between", and a red color is set when the evaluation result is "not good".

At step SA3, when the normalized value of the individual A, the cumulative rate of the calculated value of the individual A, or the converted value of the individual A (hereinafter, "evaluated value") is output as the evaluation result, the setting unit 102*f* may set the color that corresponds to the evaluated value by executing, for example, a method in which the continuous color is correlated with real numbers from 0 to 1 by using the color universal design of red (#ff2800), yellow (#faf500), and blue (#0041ff) (for example, render function prepared by an R language (see, for example, the source codes below)). Namely, on the basis of the evaluated value, the color classification may be done with continuous color tone.

```
cols=colorRamp(c("#ff2800", "#faf500", "#0041ff"))
plot(NULL, xlim=c(0, 100), ylim=c(0,1), axes=FALSE,
    xlab=" ", ylab=" ")
rect(0:99, 0, 1:100, 1, col=rgb(cols(0:99/99)/255),
    border=NA)
```

The first result data preparing unit 102g prepares the result data displayed by tiles with regard to the rectangular area of each item (for example, the pdf data with regard to the area MA described in FIG. 15), in which the color of the area is set as the setting unit 102f sets (blue, yellow, or red) and a character string corresponding to the item in the area (for example, the character string of "growth potential") is disposed. In FIG. 15, an example is described in which patterns are set instead of the colors in each tile (dot pattern: blue, oblique lines: red, and horizontal lines: yellow).

Here, when the 3 items are evaluated at step SA3, the result data displayed by tiles with regard to the 3 items may be prepared by the method described above.

Step SA5: Acquisition of Recommendable Amino Acid

When the evaluation result of "not good" is included in the evaluation results of the 9 items obtained at step SA3, the acquiring unit 102i acquires the recommendable amino acid corresponding to the item of "not good" in the evaluation result from the recommendable amino acid data file 106g.

When the 3 items are evaluated at step SA3, the recommendable amino acid corresponding to the item of "not good" in the evaluation result may be acquired from the recommendable amino acid data file 106g.

Step SA6: Preparation of Opinion Data

On the basis of the evaluation results of the 9 items obtained at step SA3, the opinion data preparing unit 102k prepares the opinion data in each item with regard to improvement of the rearing condition of the individual in the farm Y. For example, when the evaluation result is "good", the opinion data preparing unit 102k prepares the opinion data (text data) with regard to the item corresponding to this evaluation result, saying, for example, "rearing condition is excellent"; when the evaluation result is "in-between", the opinion data (text data) with regard to the item corresponding to this evaluation result is prepared, saying, for example, "there is no problem in the rearing condition"; and when the evaluation result is "not good", the opinion data (text data) with regard to the item corresponding to this evaluation result is prepared, saying, for example, "let's improve the rearing condition".

Here, when the 3 items are evaluated at step SA3, the opinion data with regard to the 3 items may be prepared by the method described above.

Step SA7: Transmission of the Data

The transmitting unit 102m transmits to the client apparatus 200 of the farmer X the result data with regard to the tile display prepared at step SA4, the data with regard to the recommendable amino acid obtained at step SA5, and the opinion data prepared at step SA6.

Step SA8: Preparation and Transmission of the Ordering Data

The ordering data preparing unit 102j prepares the ordering data with regard to the recommendable amino acid obtained at step SA5, and the transmitting unit 102m transmits the ordering data thus prepared to the client apparatus 200 of a company that sells the amino acid.

Explanation of an example of the processes that are carried out by the present system is over here.

3. Other Embodiments

In addition to the embodiments described above, the information processing method, the calculating method, the information processing apparatus, the calculating apparatus, the information processing program, and the calculating program according to the present invention can be practiced in various different embodiments within the technological scope of the claims.

Of the processings described in the embodiments, all or a part of the processings described as automatically performed ones may be manually performed, or all or a part of the processings described as manually performed ones may be also automatically performed by known methods.

In addition, the processing procedures, the control procedures, the specific names, the information including registered data of various processings and parameters such as retrieval conditions, the screen examples, and the database configuration shown in the description and the drawings may be arbitrarily modified unless otherwise specified.

The components of apparatuses constituting the present system shown in the figures are functionally conceptual and therefore not be physically configured as shown in the figures.

For example, for the operational functions provided in the server apparatus 100, in particular, for the operational functions performed in the control unit 102, all or part thereof may be implemented by the CPU and programs interpreted and executed in the CPU, or may be implemented by wired-logic hardware. The program is recorded in a non-transitory tangible computer-readable recording medium including programmed instructions for making an information processing apparatus execute the information processing method or the calculating method according to the present invention, and is mechanically read as needed by the server apparatus 100. More specifically, computer programs to give instructions to the CPU in cooperation with the OS to perform various processes are recorded in the storage unit 106 such as ROM or a HDD (hard disk drive). The computer programs are executed by being loaded to RAM, and form the control unit in cooperation with the CPU.

The computer programs may be stored in an application program server connected to the server apparatus 100 via an arbitrary network, and all or part thereof can be downloaded as necessary.

The information processing program and the calculating program according to the present invention may be stored in the non-transitory tangible computer-readable recording medium, or can be configured as a program product. The "recording medium" mentioned here includes any "portable physical medium" such as a memory card, a USB (universal serial bus) memory, an SD (secure digital) card, a flexible disk, a magneto-optical disc, ROM, EPROM (erasable programmable read only memory), EEPROM (registered trademark) (electronically erasable and programmable read only memory), CD-ROM (compact disk read only memory), MO (magneto-optical disk), DVD (digital versatile disk), and Blu-ray (registered trademark) Disc.

The "program" mentioned here is a data processing method described in an arbitrary language or description method, and therefore any form such as a source code and a binary code is acceptable. The "program" is not necessarily limited to a program configured as a single unit, and, therefore, includes those dispersively configured as a plurality of modules and libraries and those in which the function of the program is achieved in cooperation with separate programs represented as OS. Any known configuration and procedures can be used as a specific configuration and reading procedure to read a recording medium by each apparatus shown in the embodiments, an installation procedure after the reading, and the like.

The various databases and the like stored in the storage unit 106 is a storage unit such as a memory device such as RAM and ROM, a fixed disk drive such as a hard disk, a flexible disk, or an optical disc. The storage unit 106 stores therein various programs, tables, databases, files for Web pages, and the like used to perform various processes and to provide Web sites.

The server apparatus 100 may be configured as an information processing apparatus such as known personal computer and work station, or may be configured as the information processing apparatus connected to an arbitrary peripheral device. The server apparatus 100 may be provided by installing software (including the programs and the data, etc.) to cause the information processing apparatus to implement the information processing method or the calculating method according to the present invention.

Furthermore, a specific configuration of dispersion or integration of the apparatuses is not limited to the shown one. The apparatuses can be configured by functionally or physically dispersing or integrating all or part of the apparatuses in arbitrary units according to various types of additions or the like or according to functional loads. In other words, the embodiments may be implemented in arbitrary combinations thereof or an embodiment may be selectively implemented.

Other features of the invention will become apparent in the course of the following descriptions of exemplary embodiments which are given for illustration of the invention and are not intended to be limiting thereof.

EXAMPLES

Example 1

In Example 1, the correlation between each amino acid and the indicator of each item was analyzed. The pig group A (47 pigs) and the pig group B (39 pigs) in plural farms were studied. The blood samples of the pigs in the artificial lactation period were taken. From the blood samples thus obtained, by using the amino acid analysis method described in the embodiment, 20 kinds of amino acids (Ala, Arg, Asn, Cit, Gln, Gly, His, Ile, Leu, Lys, Met, Orn, Phe, Pro, Ser, Thr, Trp, Tyr, Val, and Tau) as well as the 3Met-His concentration value in blood (nmol/mL) were measured. From the obtained blood samples, the biochemical indicator values such as the blood IGF-1 concentration value, the blood albumin concentration value, the blood insulin concentration value, and the Trp/Kyn ratio were measured. In addition, the Δ body length, ADFI, G:F, and the late rearing body weight were obtained as the growth indicator value of the pig.

Here, 3Met-His is the amino acid that is present only in a muscle. Because the blood concentration thereof becomes higher as decomposition of a muscle protein progresses, this is the indicator representing the amino acid requirement amount. The Δ body length is a change amount of the body length from a weaning period to an artificial lactation period; and thus, this is the indicator proportional to a growth amount in the late growth period. The late rearing body weight is the indicator representing the growing state before shipment thereof.

In the test in which the null hypothesis is made [population correlation coefficient=0], the amino acids whose correlation coefficient with the objective variable described in 1 to 9 below was significant ($p$ value is less than 0.05) were as follows. The correlation coefficients (Pearson correlation coefficient) of the following amino acids are described in Tables 1 and 2. Here, the calculations with regard to the objective variables 1, 2, 5 8, and 9 described below were carried out in the pig group A (47 pigs), and the calculations with regard to the objective variables 3, 4, 6, and 7 described below were carried out in the pig group B (39 pigs).

1. Blood IGF-1: Asn, Gly, Pro, Tyr, Lys, Ile, Leu, and Trp
2. Blood albumin: His, Arg, Tyr, Val, Lys, Ile, Leu, Phe, and Trp
3. 3Met-His: His
4. Blood insulin: Thr, Arg, Tyr, Met, Orn, and Phe
5. Trp/Kyn: Ser, Tyr, Ile, and Trp
6. ADFI: Trp
7. G:F: 3Met-His
8. Δ Body length: Pro, Tyr, Lys, Ile, Leu, and Trp
9. Late rearing body weight: Arg, Tyr, Ile, Phe, and Trp

TABLE 1

| OBJECTIVE VARIABLE | Asn | Ser | Gly | His | Thr | Arg | Pro | Tyr | Val |
|---|---|---|---|---|---|---|---|---|---|
| BLOOD IGF-1 | 0.57 | — | 0.49 | — | — | — | 0.48 | 0.55 | — |
| BLOOD ALBUMIN | — | — | — | 0.34 | — | 0.50 | — | 0.61 | 0.35 |
| 3Met-His | — | — | — | 0.48 | — | — | — | — | — |
| BLOOD INSULIN | — | — | — | — | 0.48 | 0.43 | — | 0.48 | — |
| Trp/Kyn | — | 0.41 | — | — | — | — | — | −0.38 | — |
| ADFI | — | — | — | — | — | — | — | — | — |
| G:F | — | — | — | — | — | — | — | — | — |
| ⊿ BODY LENGTH | — | — | — | — | — | — | 0.35 | 0.46 | — |
| LATE REARING BODY WEIGHT | — | — | — | — | — | 0.40 | — | 0.49 | — |

TABLE 2

| OBJECTIVE VARIABLE | Met | Orn | Lys | Ile | Leu | Phe | Trp | 3Met-His |
|---|---|---|---|---|---|---|---|---|
| BLOOD IGF-1 | — | — | 0.41 | 0.47 | 0.37 | — | 0.62 | — |
| BLOOD ALBUMIN | — | — | 0.31 | 0.42 | 0.54 | 0.41 | 0.63 | — |

TABLE 2-continued

| OBJECTIVE VARIABLE | Met | Orn | Lys | Ile | Leu | Phe | Trp | 3Met-His |
|---|---|---|---|---|---|---|---|---|
| 3Met-His | — | — | — | — | — | — | — | 1.00 |
| BLOOD INSULIN | 0.34 | 0.37 | — | — | — | 0.45 | — | — |
| Trp/Kyn | — | — | — | −0.34 | — | — | −0.62 | — |
| ADFI | — | — | — | — | — | — | 0.36 | — |
| G:F | — | — | — | — | — | — | — | 0.42 |
| ⊿BODY LENGTH | — | — | 0.30 | 0.29 | 0.32 | — | 0.53 | — |
| LATE REARING BODY WEIGHT | — | — | — | 0.33 | — | 0.35 | 0.33 | — |

Example 2

The sample data used in Example 1 were used. By using the variable covering method, 2 or more and 6 or less variables were selected from the 20 kinds of amino acids and 3Met-His; and in view of relation with the objective variables described in 1 to 9 before, the multiple regression equation with the lowest Akaike information criterion was selected. As a result, the index formulae 1 to 9 described below were selected (each number of the index formulae corresponds to the number of the objective variable described in Example 1). The correlation coefficients of the index formulae as well as the correlation coefficients (p value of less than 0.05) are described in Table 3. The correlation coefficients of the index formulae described below using plural amino acids as the variable showed higher correlation coefficients than those of each of the single amino acids described in Tables 1 and 2. Accordingly, it was found that the index formulae described below are useful for evaluation of the pig in a farm with regard to the growth potential, the nutrition state of a protein, the utilization efficiency of an amino acid, the glucose metabolism, the stress, the appetite, the feed efficiency, the growth speed, and the growth prediction, and thus, are useful for evaluation of the nutrition state, the growth, and the physiological response of the pig in a farm.

$$\text{"}a_1 \times \text{Lys} + b_1 \times \text{Arg} + c_1 \times \text{Pro} + d_1 \times \text{Ile} + e_1 \times \text{Asn} + f_1 \times \text{Trp} + g_1\text{"} \quad \text{Index Formula 1}$$

$$\text{"}a_2 \times \text{Trp} + b_2 \times \text{Pro} + c_2 \times \text{Leu} + d_2 \times \text{Ala} + e_2 \times \text{Gln} + f_2 \times \text{Asn} + g_2\text{"} \quad \text{Index Formula 2}$$

$$\text{"}a_3 \times \text{His} + b_3 \times \text{Ser} + c_3 \times \text{Thr} + d_3 \times \text{Gln} + e_3 \times \text{Leu} + f_3 \times \text{Val} + g_3\text{"} \quad \text{Index Formula 3}$$

$$\text{"}a_4 \times \text{His} + b_4 \times \text{Lys} + c_4 \times \text{Thr} + d_4 \times \text{Pro} + e_4 \times \text{Met} + f_4 \times \text{Gly} + g_4\text{"} \quad \text{Index Formula 4}$$

$$\text{"}a_5 \times \text{Asn} + b_5 \times \text{Ser} + c_5 \times \text{Orn} + d_5 \times \text{Phe} + e_5 \times \text{Trp} + f_5\text{"} \quad \text{Index Formula 5}$$

$$\text{"}a_6 \times \text{Phe} + b_6 \times \text{Val} + c_6 \times \text{Tau} + d_6 \times \text{Leu} + e_6 \times \text{Tyr} + f_6 \times \text{Trp} + g_6\text{"} \quad \text{Index Formula 6}$$

$$\text{"}a_7 \times \text{Asn} + b_7 \times \text{Ser} + c_7 \times \text{"3Met-His"} + d_7 \times \text{Met} + e_7 \times \text{Orn} + f_7 \times \text{Phe} + g_7\text{"} \quad \text{Index Formula 7}$$

$$\text{"}a_8 \times \text{Trp} + b_8 \times \text{Gln} + c_8 \times \text{Ala} + d_8 \times \text{Gly} + e_8 \times \text{Pro} + f_8 \times \text{Val} + g_8\text{"} \quad \text{Index Formula 8}$$

$$\text{"}a_9 \times \text{Ala} + b_9 \times \text{Pro} + c_9 \times \text{Ile} + d_9 \times \text{Trp} + e_9 \times \text{Gly} + f_9 \times \text{Gln} + g_9\text{"} \quad \text{Index Formula 9}$$

In Index Formula 1, $a_1$, $b_1$, $c_1$, $d_1$, $e_1$, and $f_1$ each are a real number other than zero, and $g_1$ is a real number.
In Index Formula 2, $a_2$, $b_2$, $c_2$, $d_2$, $e_2$, and $f_2$ each are a real number other than zero, and $g_2$ is a real number.
In Index Formula 3, $a_3$, $b_3$, $c_3$, $d_3$, $e_3$, and $f_3$ each are a real number other than zero, and $g_3$ is a real number.

In Index Formula 4, $a_4$, $b_4$, $c_4$, $d_4$, $e_4$, and $f_4$ each are a real number other than zero, and $g_4$ is a real number.
In Index Formula 5, $a_5$, $b_5$, $c_5$, $d_5$, and $e_5$ each are a real number other than zero, and $f_5$ is a real number.
In Index Formula 6, $a_6$, $b_6$, $c_6$, $d_6$, $e_6$, and $f_6$ each are a real number other than zero, and $g_6$ is a real number.
In Index Formula 7, $a_7$, $b_7$, $c_7$, $d_7$, $e_7$, and $f_7$ each are a real number other than zero, and $g_7$ is a real number.
In Index Formula 8, $a_8$, $b_8$, $c_8$, $d_8$, $e_8$, and $f_8$ each are a real number other than zero, and $g_8$ is a real number.
In Index Formula 9, $a_9$, $b_9$, $c_9$, $d_9$, $e_9$, and $f_9$ each are a real number other than zero, and $g_9$ is a real number.

TABLE 3

| OBJECTIVE VARIABLE | INDEX FORMULA | CORRELATION COEFFICIENT BETWEEN OBJECTIVE VARIABLE AND INDEX FORMULA VALUE |
|---|---|---|
| BLOOD IGF-1 | INDEX FORMULA 1 | r 0.83 |
| BLOOD ALBUMIN | INDEX FORMULA 2 | r 0.77 |
| 3Met-His | INDEX FORMULA 3 | r 0.80 |
| BLOOD INSULIN | INDEX FORMULA 4 | r 0.88 |
| Trp/Kyn | INDEX FORMULA 5 | r 0.79 |
| ADFI | INDEX FORMULA 6 | r 0.70 |
| G:F | INDEX FORMULA 7 | r 0.54 |
| ⊿ BODY LENGTH | INDEX FORMULA 8 | r 0.73 |
| LATE REARING BODY WEIGHT | INDEX FORMULA 9 | r 0.74 |

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed is:

1. An information processing method comprising:

evaluating growth of an animal, by evaluating a growth prediction using a value of index formula (9), wherein the value is calculated by substituting a blood concentration value of the amino acids Ala, Pro, Ile, Trp, Gly, and Gln obtained from the animal into index formula (9) to produce an evaluation result of the growth prediction $$a_9 \times Ala + b_9 \times Pro + c_9 \times Ile + d_9 \times Trp + e_9 \times Gly + f_9 \times Gln + g_9 \qquad (9)$$

where $a_9$, $b_9$, $c_9$, $d_9$, $e_9$, and $f_9$ each are a real number other than zero, and $g_9$ is a real number, determining, based on the evaluation result of the growth prediction, a need to improve the growth of the animal, acquiring, following the determining, information regarding a recommendable amino acid comprising an amino acid recommended to improve the evaluation result of the growth prediction from a database, and administering the recommendable amino acid obtained based on the information acquired by the acquiring step to the animal in order to improve the growth, wherein the evaluating and the acquiring are carried out in a control unit of an information processing apparatus comprising the control unit, at the administering, at least one restriction amino acid selected from the group consisting of Lys, Met, Thr, Gly, Cyst, and His is administered to the animal with the recommendable amino acid, and the animal is a pig and the blood concentration value is of a daily age of the pig of 45 days to 60 days.

2. The information processing method according to claim 1, wherein the evaluating growth of the animal further comprises, evaluating growth speed using a value of index formula (8), wherein the value is calculated by substituting a blood concentration value of the amino acids Trp, Gln, Ala, Gly, Pro, and Val obtained from the animal into the index formula (8) to produce an evaluation result of the growth speed $$a_8 \times Trp + b_8 \times Gln + c_8 \times Ala + d_8 \times Gly + e_8 \times Pro + f_8 \times Val + g_8 \qquad (8)$$

where $a_8$, $b_8$, $c_8$, $d_8$, $e_8$, and $f_8$ each are a real number other than zero, and $g_8$ is a real number, the determining is further based on the evaluation result of the growth speed, and the recommendable amino acid further comprises an amino acid recommended to improve the evaluation result of the growth speed which is at least one selected from the group consisting of Trp, Gln, Ala, Gly, Pro, and Val.

3. The information processing method according to claim 1, comprising:

setting a color, a pattern, or a combination thereof corresponding to the evaluation result of the growth prediction; and preparing a first result data with regard to a tile display of a rectangular area, in which the color, the pattern, or a combination thereof in the area are those having been set at the setting and a character string corresponding to the evaluation result of the growth prediction is disposed in the area, wherein the setting and the preparing the first result data are carried out in the control unit.

4. The information processing method according to claim 1, comprising preparing a second result data with regard to the evaluation results of the growth prediction, wherein the evaluation result is displayed in a table style or in a list style, wherein the preparing the second result data is carried out in the control unit.

5. The information processing method according to claim 1, wherein the database comprises, as the recommendable amino acid, at least one amino acid selected from the group consisting of Met, Lys, Thr, Trp, Val, Leu, Ile, Arg, Tyr, Phe, Gln, Glu, Gly, Cys2, and His.

6. The information processing method according to claim 1, wherein the information processing apparatus is connected through a communicable network to an information processing apparatus of a company that sells amino acids, wherein the method comprises:

preparing ordering data of the recommendable amino acid based on the information acquired at the acquiring; and transmitting the ordering data prepared at the preparing ordering data to the information processing apparatus of the company, wherein the preparing ordering data and the transmitting ordering data are carried out in the control unit.

7. The information processing method according to claim 1, comprising preparing an opinion data, on the basis of the evaluation result of the growth prediction, opinion data regarding options for improving a growth prediction of other animals reared in a rearing condition of the animal, wherein the preparing opinion data is carried out in the control unit.

8. The information processing method according to claim 1, wherein the evaluating further comprises evaluating stress, and the evaluating stress is carried out by using a blood concentration value of at least one amino acid selected from the group consisting of Ser, Tyr, Ile, and Trp, or a value of a formula that comprises an explanatory variable to be substituted with the blood concentration value, calculated using the formula and the blood concentration value.

9. The information processing method according to claim 1, wherein the administering further administers the recommendable amino acid obtained based on the information acquired by the acquiring to an animal raised in a same rearing environment as the animal.

10. An information processing apparatus comprising a control unit, wherein the control unit comprises:

an evaluating unit that evaluates growth of an animal, by evaluating a growth prediction using a value of index formula (9), wherein the value is calculated by substituting a blood concentration value of the amino acids Ala, Pro, Ile, Trp, Gly, and Gln obtained from the animal into index formula (9) to produce an evaluation result of growth prediction $$a_9 \times Ala + b_9 \times Pro + c_9 \times Ile + d_9 \times Trp + e_9 \times Gly + f_9 \times Gln + g_9 \qquad (9)$$

where $a_9$, $b_9$, $c_9$, $d_9$, $e_9$, and $f_9$ each are a real number other than zero, and $g_9$ is a real number, and determines, based on the evaluation result of the growth prediction, a need to improve the growth of the animal, an acquiring unit that acquires, following the determining, information regarding a recommendable amino acid comprising an amino acid recommend to improve the evaluation result of the growth prediction from a database, and an administering unit that administers the recommendable amino acid obtained based on the information acquired by the acquiring unit to the animal in order to improve the growth, wherein the administering unit administers at least one restriction amino acid selected from the group consisting of Lys, Met, Thr, Gly, Cyst, and His to the animal with the recommendable amino acid, and (III) the animal is a pig and the blood concentration value is of a daily age of the pig of 45 days to 60 days.

11. The information processing apparatus according to claim 10, wherein the evaluating unit further evaluates growth speed by using a value of index formula (8), wherein the value is calculated by substituting a blood concentration value of the amino acids Trp, Gln, Ala, Gly, Pro, and Val obtained from the animal into the index formula (8) to produce an evaluation result of the growth speed $$a_8 \times Trp + b_8 \times Gln + c_8 \times Ala + d_8 \times Gly + e_8 \times Pro + f_8 \times Val + g_8 \qquad (8)$$

where $a_8$, $b_8$, $c_8$, $d_8$, $e_8$, and $f_8$ each are a real number other than zero, and $g_8$ is a real number, the evaluating unit further determines based on the evaluation result of the growth speed, and the recommendable amino acid further comprises an amino acid recommended to improve the evaluation result of the growth speed which is at least one selected from the group consisting of Trp, Gln, Ala, Gly, Pro, and Val.

12. The information processing apparatus according to claim 10, wherein the control unit comprises:

a setting unit that sets a color, a pattern, or a combination thereof corresponding to the evaluation result of the growth prediction; and a first result data preparing unit that prepares a first result data with regard to a tile display of a rectangular area, in which the color, the pattern, or a combination thereof in the area are those having been set by the setting unit and a character string corresponding to the growth prediction is disposed in the area.

13. The information processing apparatus according to claim 10, wherein the control unit comprises a second result data preparing unit that prepares a second result data with regard to the evaluation results of the growth prediction, wherein the evaluation result is displayed in a table style or in a list style.

14. The information processing apparatus according to claim 10, wherein the database comprises, as the recommendable amino acid, at least one amino acid selected from the group consisting of Met, Lys, Thr, Trp, Val, Leu, Ile, Arg, Tyr, Phe, Gln, Glu, Gly, Cys2, and His.

15. The information processing apparatus according to claim 10, being connected through a communicable network to an information processing apparatus of a company that sells amino acids, wherein the control unit comprises:

an ordering data preparing unit that prepares ordering data of the recommendable amino acid based on the information acquired by the acquiring unit; and an ordering data transmitting unit that transmits the ordering data prepared by the ordering data preparing unit to the information processing apparatus of the company.

16. The information processing apparatus according to claim 10, wherein the control unit comprises an opinion data preparing unit that prepares, on the basis of the evaluation result of the growth prediction, opinion data regarding options for improving a growth prediction of other animals reared in a rearing condition of the animal.

17. The information processing apparatus according to claim 10, wherein the evaluating unit further evaluates stress, and the evaluating unit evaluates stress by using a blood concentration value of at least one amino acid selected from the group consisting of Ser, Tyr, Ile, and Trp, or a value of a formula that comprises an explanatory variable to be substituted with the blood concentration value, calculated using the formula and the blood concentration value.

18. The information processing apparatus according to claim 10, wherein the administering further comprises administering the recommendable amino acid obtained based on the information acquired by the acquiring to an animal raised in a same rearing environment as the animal.

19. An information processing program product having a non-transitory tangible computer readable medium comprising programmed instructions for causing a control unit of an information processing apparatus comprising the control unit to carry out an information processing method, wherein the information processing method comprises:

evaluating growth of an animal, by evaluating a growth prediction using a value of index formula (9), wherein the value is calculated by substituting a blood concentration value of the amino acids Ala, Pro, Ile, Trp, Gly, and Gln obtained from the animal into index formula (9) to produce an evaluation result of the growth prediction $$a_9 \times Ala + b_9 \times Pro + c_9 \times Ile + d_9 \times Trp + e_9 \times Gly + f_9 \times Gln + g_9 \qquad (9)$$

where $a_9$, $b_9$, $c_9$, $d_9$, $e_9$, and $f_9$ each are a real number other than zero, and $g_9$ is a real number, determining, based on the evaluation result of the growth prediction, a need to improve the growth of the animal, acquiring, following the determining, information regarding a recommendable amino acid comprising an amino acid recommended to improve the evaluation result of the growth prediction from a database, and administering the recommendable amino acid obtained based on the information acquired by the acquiring to the animal in order to improve the growth, wherein the evaluating and the acquiring are carried out in a control unit of an information processing apparatus comprising the control unit, at the administering, at least one restriction amino acid selected from the group consisting of Lys, Met, Thr, Gly, Cyst, and His is administered to the animal with the recommendable amino acid, and the animal is a pig and the blood concentration value is of a daily age of the pig of 45 days to 60 days.

20. The information processing program product of claim 19, wherein the evaluating further comprises evaluating stress, and the evaluating the stress is carried out by using a blood concentration value of at least one amino acid selected from the group consisting of Ser, Tyr, Ile, and Trp, or a value of a formula that comprises an explanatory variable to be substituted with the blood concentration value, calculated using the formula and the blood concentration value.

21. The information processing program product of claim 19, wherein the administering further administers the recommendable amino acid obtained based on the information acquired by the acquiring to an animal raised in a same rearing environment as the animal.

* * * * *